United States Patent [19]
Burlingame et al.

[11] Patent Number: 5,866,379
[45] Date of Patent: Feb. 2, 1999

[54] ENZYMATIC CONVERSION OF α-HYDROXYNITRILES TO THE CORRESPONDING α-HYDROXYAMIDES, ACIDS OR ACID SALTS

[75] Inventors: Richard P. Burlingame, Manitowoc; James R. Millis, Kohler; Fernando Sanchez-Riera, Manitowoc, all of Wis.; Thomas F. Blackburn, Chesterfield, Mo.; Alan D. Grund, Manitowoc, Wis.

[73] Assignee: Novus International, St. Louis, Mo.

[21] Appl. No.: 790,675

[22] Filed: Jan. 28, 1997

[51] Int. Cl.[6] ........................................... C12P 13/02
[52] U.S. Cl. ..................... 435/129; 435/252.1; 435/822
[58] Field of Search ..................... 435/129, 822, 435/252.1

[56] References Cited

U.S. PATENT DOCUMENTS

| | | | |
|---|---|---|---|
| 2,745,745 | 5/1956 | Blake et al. | 99/4 |
| 4,001,081 | 1/1977 | Commeyras et al. | 195/29 |
| 4,248,968 | 2/1981 | Watanabe et al. | 435/129 |
| 4,366,250 | 12/1982 | Jallageas et al. | 435/280 |
| 4,481,362 | 11/1984 | Nakai et al. | 548/498 |
| 4,497,957 | 2/1985 | Nakai et al. | 548/496 |
| 4,637,982 | 1/1987 | Yamada et al. | 435/129 |
| 4,661,456 | 4/1987 | Yamada et al. | 435/244 |
| 4,661,457 | 4/1987 | Yamada et al. | 435/244 |
| 4,851,342 | 7/1989 | Watanabe et al. | 435/129 |
| 5,130,240 | 7/1992 | Ozaki et al. | 435/116 |
| 5,135,858 | 8/1992 | Yamada et al. | 435/106 |
| 5,252,470 | 10/1993 | Ozaki et al. | 435/116 |
| 5,314,819 | 5/1994 | Yamada et al. | 435/232 |
| 5,326,702 | 7/1994 | Endo et al. | 435/129 |
| 5,334,519 | 8/1994 | Yamada et al. | 435/129 |
| 5,498,532 | 3/1996 | Katsumata et al. | 435/106 |
| 5,508,181 | 4/1996 | Hashimoto et al. | 435/129 |
| 5,559,024 | 9/1996 | Leroux et al. | 435/252.3 |
| 5,563,053 | 10/1996 | Takashima et al. | 435/122 |

FOREIGN PATENT DOCUMENTS

| | | |
|---|---|---|
| 0 348 901 | 6/1989 | European Pat. Off. . |
| 0 356 912 | 8/1989 | European Pat. Off. . |
| 0 444 640 | 2/1991 | European Pat. Off. . |
| 0 445 646 A2 | 9/1991 | European Pat. Off. . |
| 0 486 289 A2 | 5/1992 | European Pat. Off. . |
| 0 601 195 | 5/1993 | European Pat. Off. . |
| 0 610 049 A2 | 8/1994 | European Pat. Off. . |
| 0 666 320 | 1/1995 | European Pat. Off. . |
| 0 666 321 | 1/1995 | European Pat. Off. . |
| 0 713 914 | 2/1995 | European Pat. Off. . |
| 0 731 079 | 3/1996 | European Pat. Off. . |
| 60-83580 | 5/1985 | Japan . |
| 62-21519 | 5/1987 | Japan . |
| 4-40898 | 2/1992 | Japan . |
| 4-40899 | 2/1992 | Japan . |
| 719635 | 12/1954 | United Kingdom . |
| WO 80/01571 | 1/1980 | WIPO . |
| WO 86/07386 | 1/1986 | WIPO . |
| WO 92/05275 | 9/1991 | WIPO . |
| WO 94/17190 | 1/1994 | WIPO . |
| WO 95/04828 | 8/1994 | WIPO . |
| WO 95/17505 | 12/1994 | WIPO . |
| WO 96/09403 | 9/1995 | WIPO . |

OTHER PUBLICATIONS

Aimin et al. "Production and Properties of 3–Cyanopyridine Hydratase in Rhodococcus equi SHB–121" Applied Biochemistry and Biotechnology, vol. 53 (1995) pp. 65–73.

Azza et al. "Cloning of the Wide Spectrum Amidase Gene From Brevibacterium sp. R312 by Genetic Complementation. Over–expression in Brevibacterium sp. and *Escherichia coli*," FEMS Microbiology Letters, vol. 222 (1994) pp. 129–136.

Bartling et al. "Molecular Characterization of Two Cloned Nitrilases from *Arabidopsis thaliana*: Ket Enzymes in Biosynthesis of the Plant Hormone Indole–3–Acetic Acid" Proc. Natl. Acad. Sci. USA, vol. 91 (Jun. 1994) pp. 6021–6025.

Bauer et al. "Enantioselective Hydrolysis of Racemic 2–Phenylpropionitrile and Other (R, S)–2–Arylpropionitriles by a New Bacterial Isolate, *Agrobacterium tumefaciens* Strain d3" Appl. Microbiol. Biotechnol., vol. 42 (1994) pp. 1–7.

Blakey et al. "Regio– and Stero–Specific Nitrile Hydrolysis by the Nitrile Hydratase from Rhodococcus AJ270" FEMS Microbiology Letters, vol. 129 (1995) pp. 57–62.

Brennan et al. "Amidase Active Whole Cells of *Corynebacterium nitrilophilus* for Ammonium Acrylate Production" Biotechnology Letters, vol. 17, No. 5 (May 1995) pp. 513–518.

Ciskanik et al. "Purification and Characterization of an Enantioselective Amidase from Pseudomonas Chloropaphis B23" Applied and Environmental Microbiology, vol. 61, No. 3 (Mar. 1995) pp. 998–1003.

Crosby et al. "Regioselective Hydrolysis of Aromatic Dinitriles Using a Whole Cell Catalyst" J. Chem. Soc. Perkin Trans, vol. 1 (1994) pp. 1679–1687.

(List continued on next page.)

*Primary Examiner*—Herbert J. Lilling
*Attorney, Agent, or Firm*—Senniger, Powers, Leavitt & Roedel

[57] ABSTRACT

Enzymes derived from the isolated and substantially purified microorganisms of the present invention, designated herein as strains 52 and 56wt, are capable of hydrating nitriles such as 2-hydroxy-4-(methylthio)-butanenitrile (HMB-nitrile) to their corresponding amides, and further, of hydrolyzing amides such as 2-hydroxy-4-(methylthio)-butaneamide (HMB-amide) to their corresponding carboxylic acids. Advantageously, the nitrile hydratase of these strains is not substantially inhibited by the α-hydroxybutyramide product being formed; rather, this enzyme maintains the ability to hydrate an α-hydroxybutyronitrile to its corresponding amide even at high amide concentrations, including at saturating amide conditions. As such, enzymes derived from strains 52 and 56wt are particularly suited for commercial use in preparing agrichemical intermediates such as HMB-amide. HMB-amide may, in turn, be hydrolyzed through traditional or enzymatic conversion methods to form HMB-acid or salts thereof, which are useful as methionine substitutes in feeds for domestic animals.

64 Claims, 13 Drawing Sheets

OTHER PUBLICATIONS

Dubey et al. "Biological Cyanide Destruction Mediated by Microorganisms" World Journal of Microbiology & Biochemistry vol. 11 (1195) pp. 257–265.

Effenberger et al. "Enzyme–Catalysed Enantioselective Hydrolysis of Racemic Naproxen Nitrile" Bioorganic & Medicinal Chem., vol. 2, No. 7 (1994) pp. 715–721.

Fronk et al. "Oral Nicotinic Acid as a Treatment for Ketosis" Journal of Dairy Science, vol. 62 (1979) pp. 1804–1807.

Gradley et al. "Asymmetric Hydrolysis of R–(–) ,S(+)–2–methylbutyronitrile by Rhodococcus Rhodochrous NCIMB 11216" Arch Microbiol., vol. 161 (1994) 246–251.

Gradley et al. "Asymmetric Hydrolysis of Chiral Nitriles by Rhodococcus Rhodochrous NCIMB 11216 Nitrilase" Biotechnology Letters, vol. 16, No. 1 (Jan. 1994) pp. 41–46.

Hall et al. "Acquisition of New Metabolic Activities by Microbial Populations" Methods in Enzymology, vol. 224 (1993) pp. 603–613.

Honda et al. "Spectroscopic Observation of the Intramolecular Electron Transfer in the Photoactivation Process of Nitrile Hydratase" Biochemistry, vol. 33 (1994) pp. 3577–3583.

Ishikawa et al. "Microbial Conversion of DL–5–Substituted Hydantoins to the Corresponding L–Amino Acids by Bacillus Stearothermophilus NS1122A" Biosci. Biotech. Biochem., vol. 58. No. 2 (1994) pp. 265–270.

Kobayashi et al. "Versatile Nitrilases: Nitrile–Hydrolysing Enzymes" FEMS Microbio. Letters, vol. 120 (1994) pp. 217–224.

Kobayashi et al. "Enzymatic Synthesis of Acrylamide: A Success Story Not Yet Over" Trends in Biotech., pp. 402–408.

Kobayashi et al. "Occurrence of Enzymes Involved in Biosynthesis of Indole–3–acetic Acid From Indole–3–Acetonitrile in Plant–Associated Bacteria, Agrobacterium and Rhizobium" Proc. Natl. Acad. Sci. USA, vol. 92 (Jan. 1995) pp. 714–718.

Kunz et al. "Alternative Routes of Enzymic Cyanide Metabolism in Pseudomonas Fluorescens NCIMB 11764" Microbiology, vol. 140 (1994) pp. 1705–1712.

Layh et al. "Enantioselective Hydrolysis of Racemic Naproxen Nitrile and Naproxen Amide to S–Naproxen by New Bacterial Isolates" J. of Biotechnology, vol. 33 (1994) pp. 175–182.

M. D. Lilly "Advances in Biotransformation Processes" Chem. Eng. Sci., vol. 49, No. 2 (1994) pp. 151–159.

Masutomo et al. "Enantioselective Hydrolysis of (RS)–2–Iso–propyl–4'–Chlorophenylacetonitrile by Pseudomonas sp. B21C9"Biosci. Biotech. Biochem., vol. 59 No. 4 (1995) pp. 720–722.

Moreau et al. "Application of High–Performance Liquid Chromatography to the Study of the Biological Transformation of Adiponitrile" Journal of Chromatography B, vol. 656 (1994) pp. 197–202.

O'Grady et al. "Isolation of A Novel Agrobacterium spp Capable of Degrading a Range of Nitrile Compounds" Biotech. Letters, vol. 16, No. 1 (Jan. 1994) pp. 47–50.

van der Werf et al. "The Potential of Lyases for the Industrial Production of Optically Active Compounds" Trends in Biotech., vol. 12 (1994) pp. 95–103.

N. J. Turner "Recent Advances in the Use of Enzyme–Catalysed Reactions in Organic Synthesis" Natural Product Reports, (1994) pp. 1–15.

Warhurst et al. "Biotransformations Catalyzed by the Genus Rhodococcus" Critical Reviews in Biotechnology, vol. 14, No. 1 (1994) pp. 29–73.

Yohda et al. "Molecular Cloning & Nucleotide Sequence of the Gene Coding Photosensitive Nitrile Hydratase" pp. 158–159.

R. Endo et al. "Fermentative Manufacture of α–hydroxy–4–methylthiobutylamide" Chemical Abstracts, vol. 117, No. 5, Abstract No. 46744h (Aug. 3, 1992) pp. 763–764.

R. Endo et al. "Fermentative Manufacture of α–hydroxy–4–methylthiobutyric acid" Chemical Abstracts, vol. 116, No. 25, Abstract No. 254675x (Jun. 22, 1992) p. 657.

T. Nagasawa et al. "Large–Scale Bioconversionof Nitriles into Useful Amides and Acids" Biocatalysis, Chapter 14, Van Nostrand Reinhold Catalysis Series, Van Nostrand Reinhold, NY (1990) pp. 277–318.

V. Okano et al. "Kinetic Secondary Deuterium Isotope Effects for Substituted Benzaldehyde Cyanohydrin Formation"Journal of the American Chemical Society, vol. 98, No. 13 (1976).

Grant & Hackh's Chemical Dictionary, Fifth Edition, McGraw–Hill, Inc. (1987) p. 519.

Hawley's Condensed Chemical Dictionary, Thirteenth Edition, Van Nostrand Reinhold (1997) p. 984.

2 HOURS

A DODECANE
B HMB-NITRILE
C HMB-ACID
D HMB-AMIDE

8 HOURS

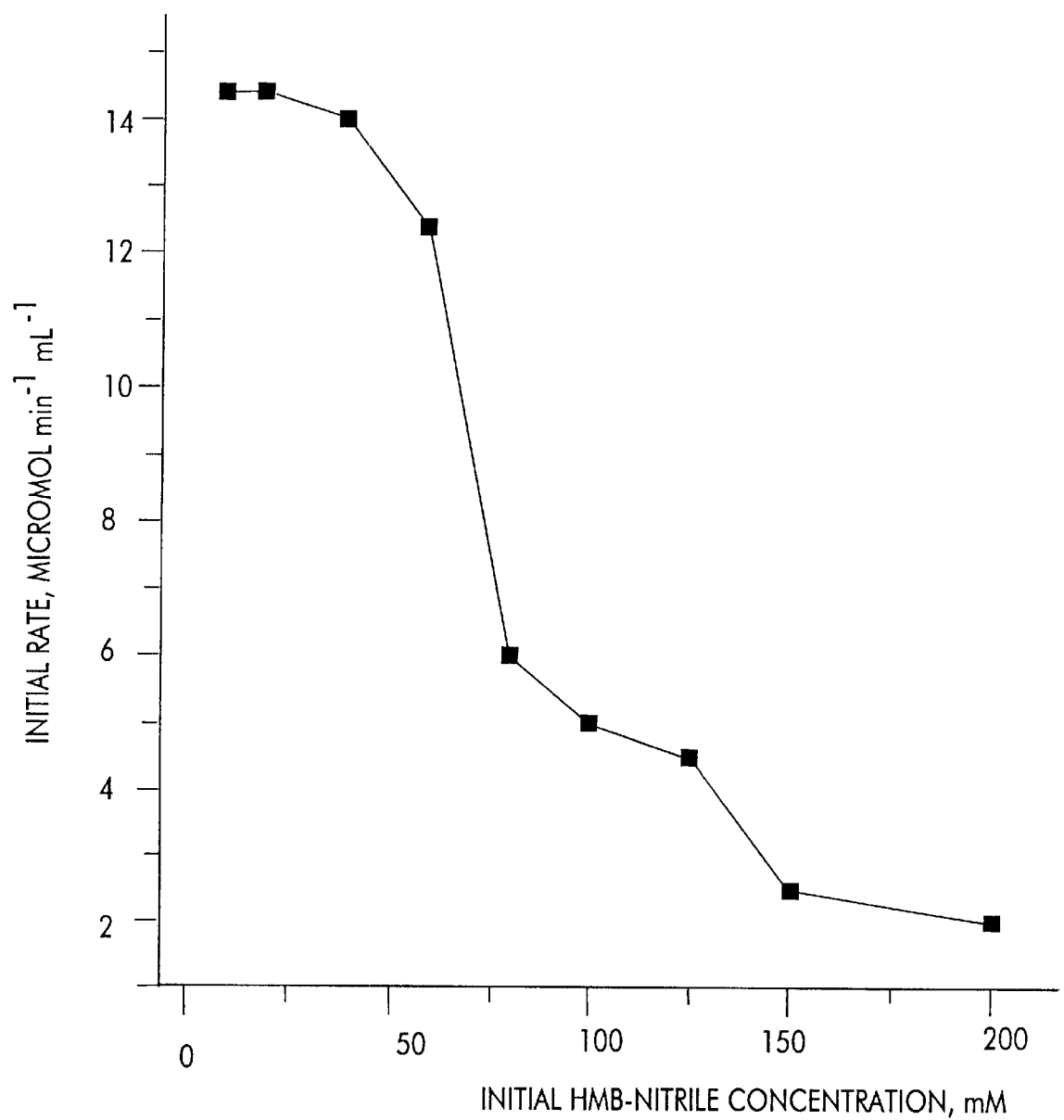

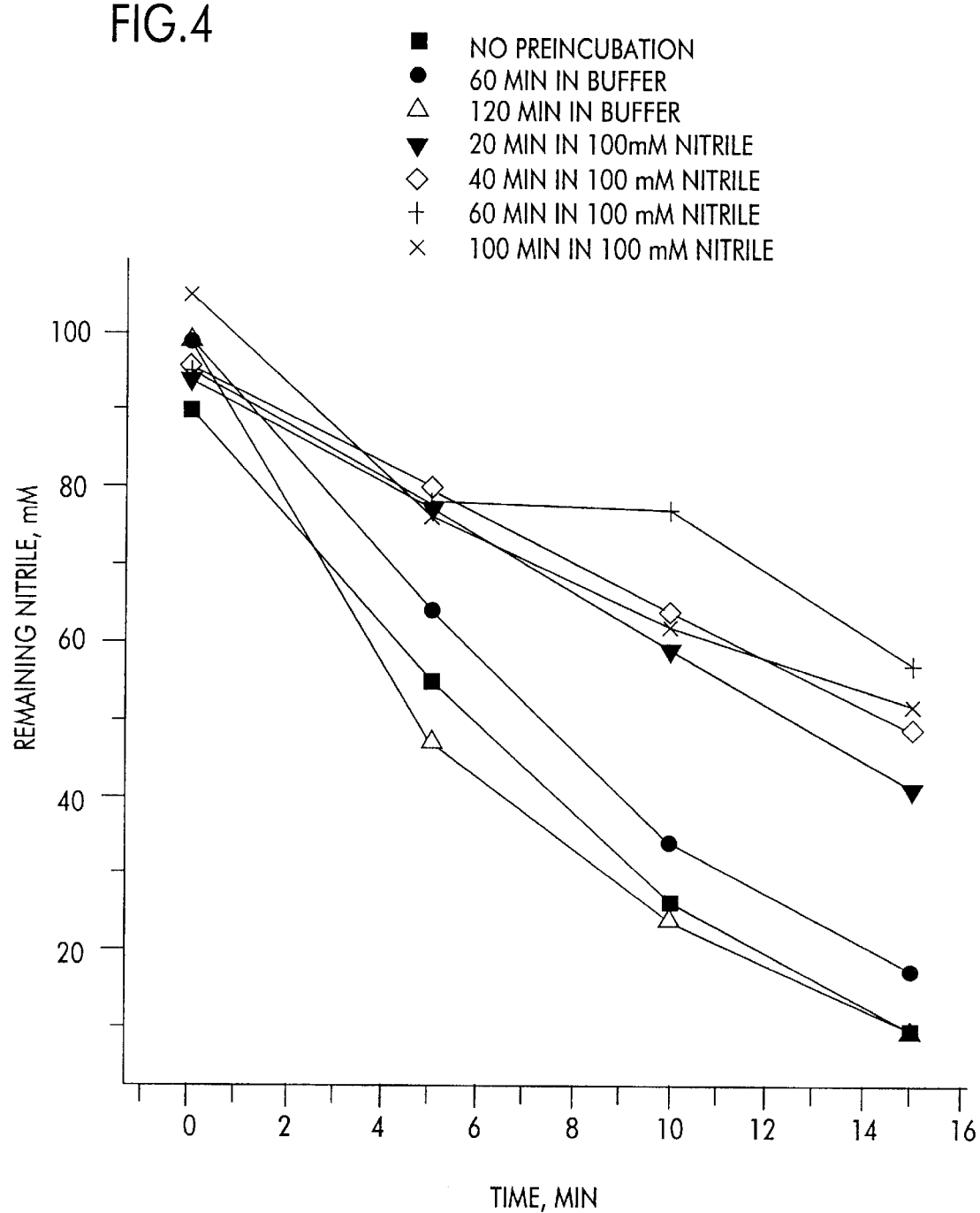

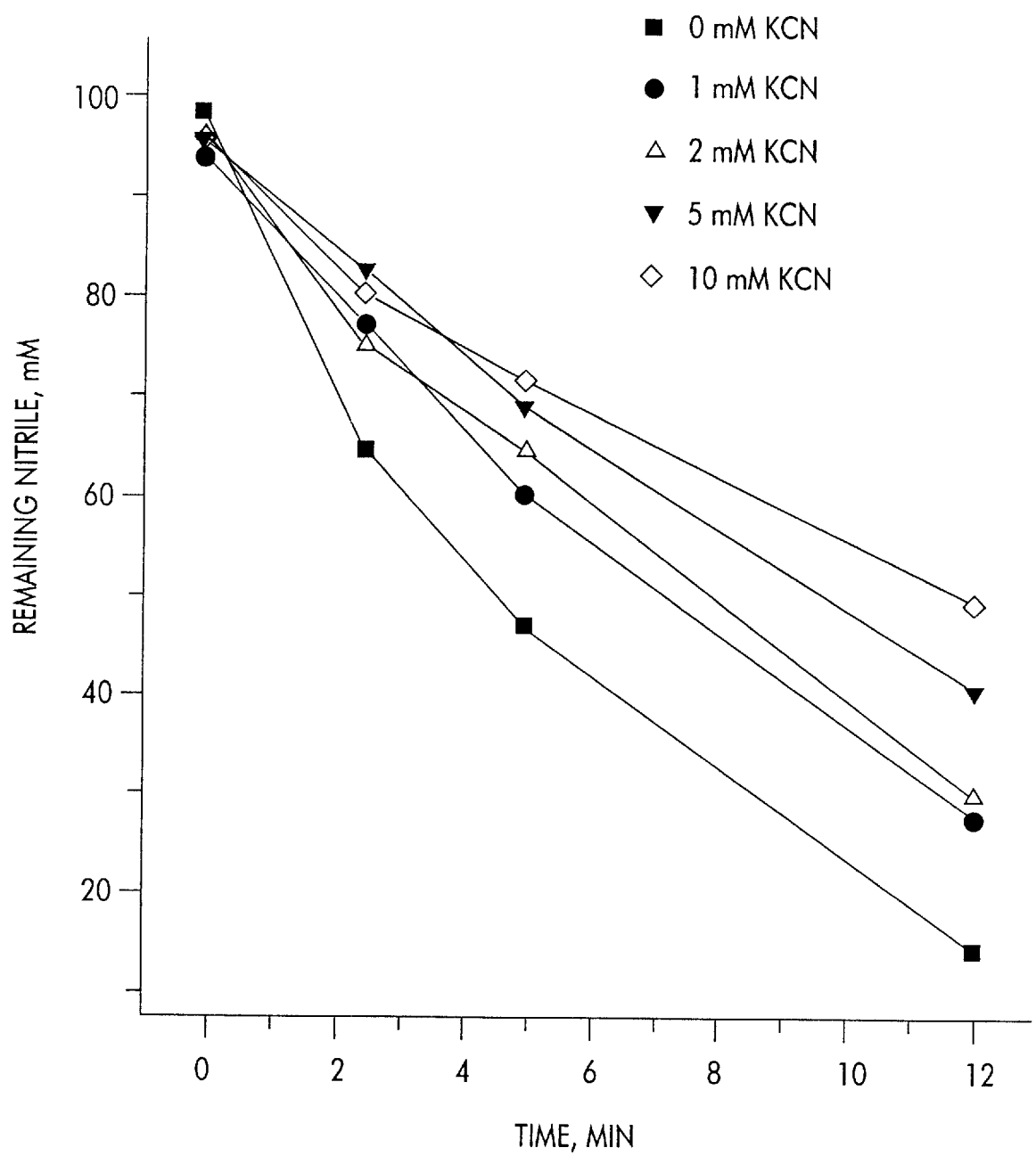

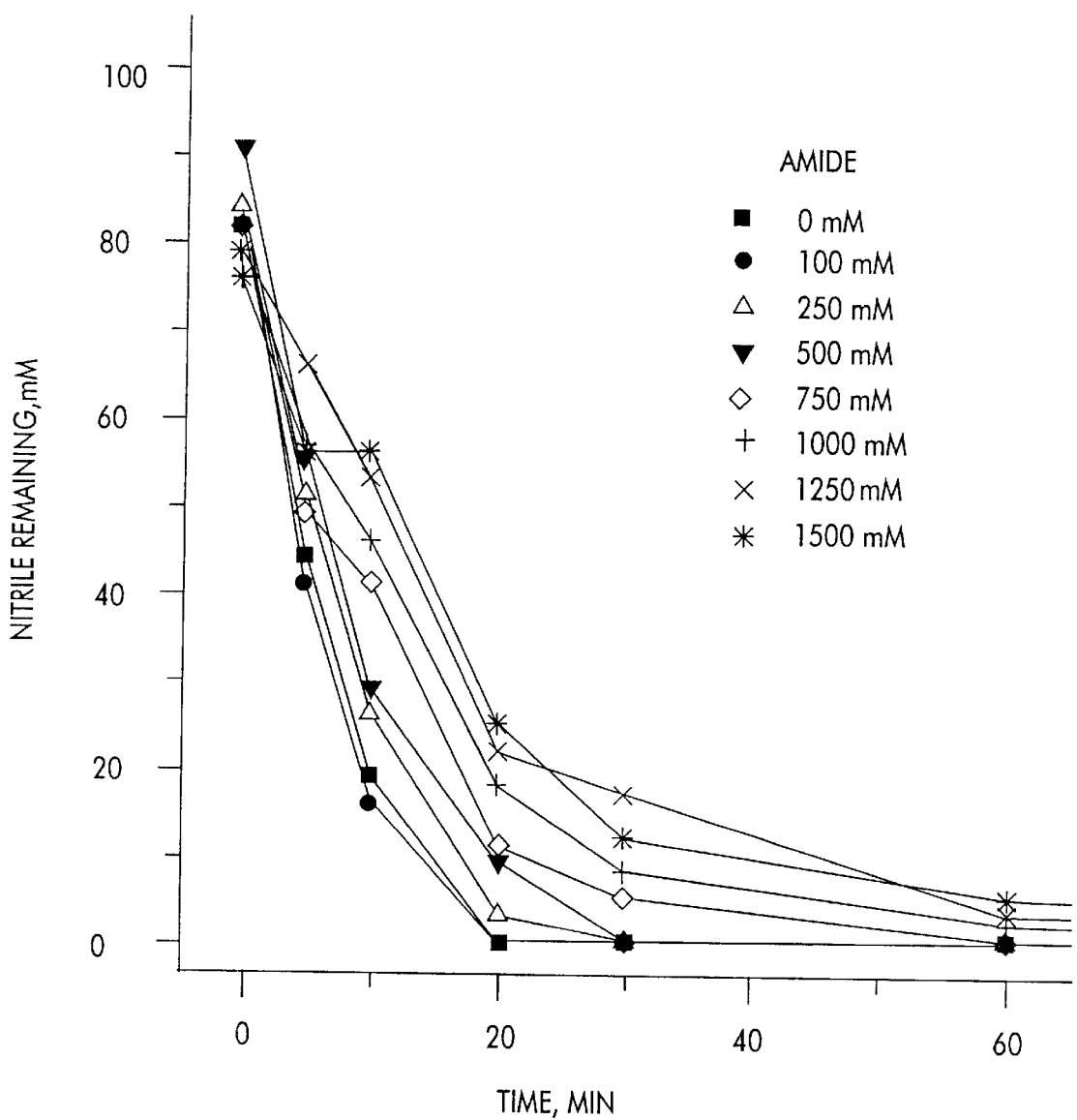

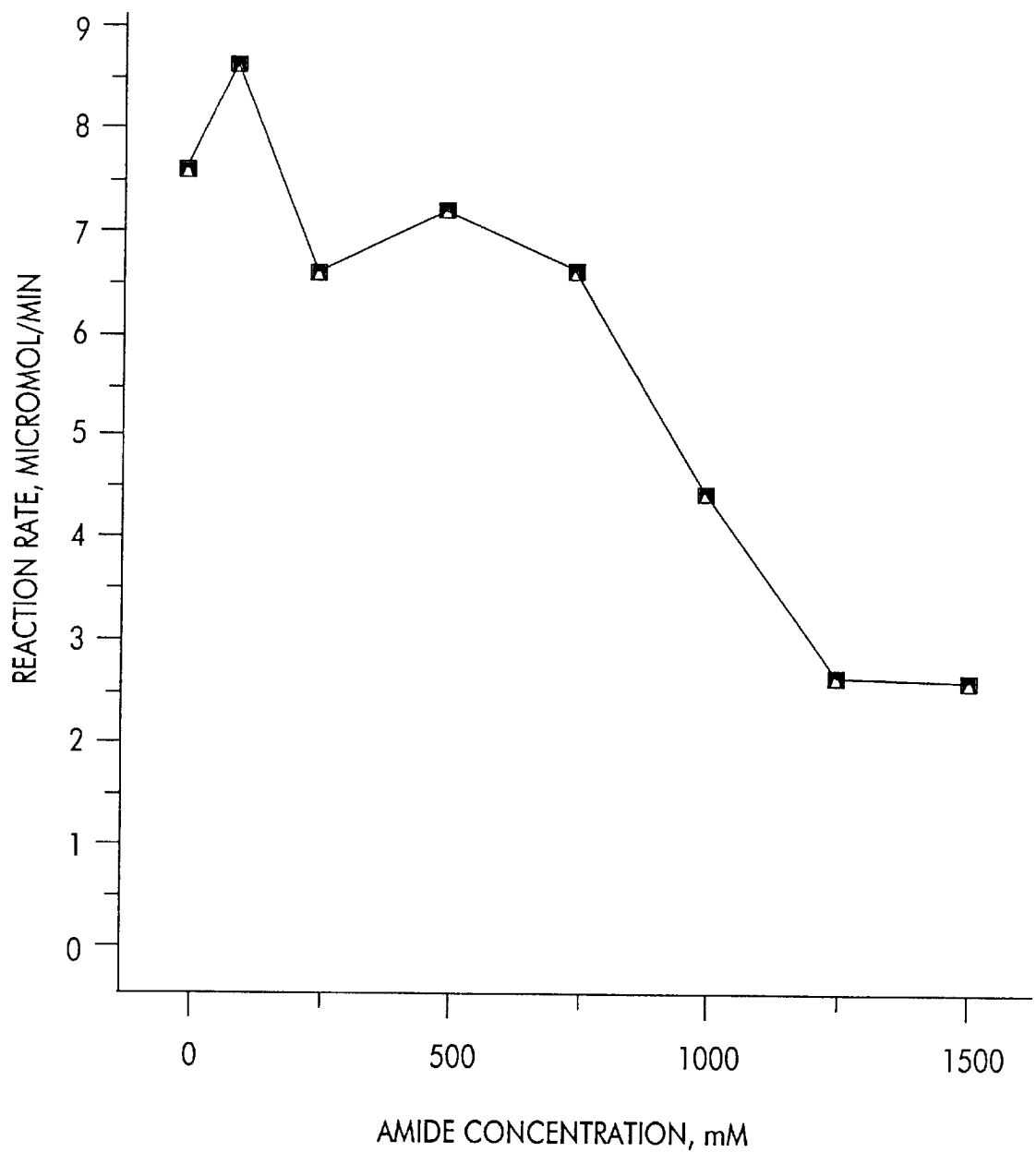

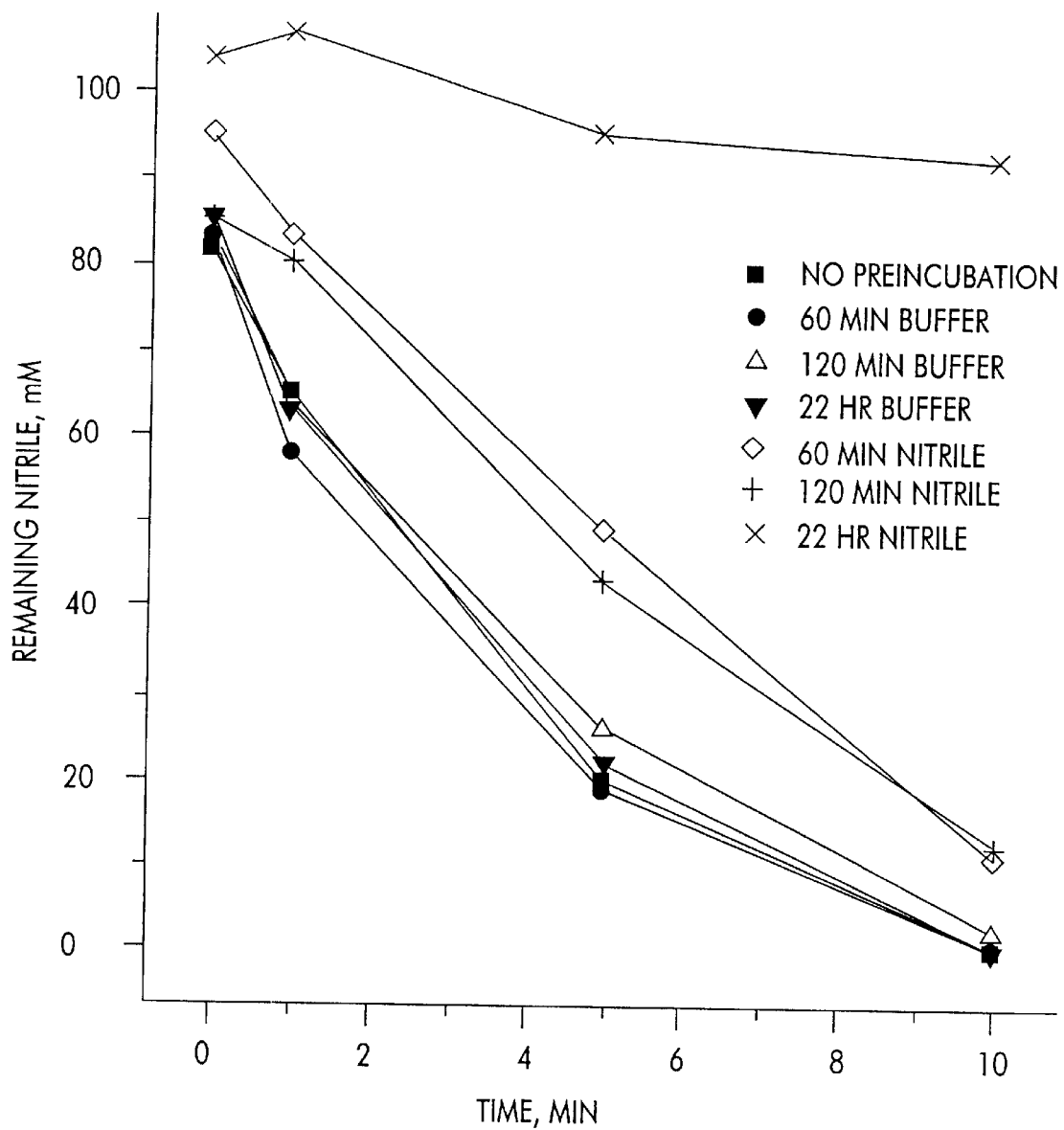

ms
ENZYMATIC CONVERSION OF α-HYDROXYNITRILES TO THE CORRESPONDING α-HYDROXYAMIDES, ACIDS OR ACID SALTS

BACKGROUND OF THE INVENTION

The present invention generally relates to the preparation of α-hydroxyamides or α-hydroxy carboxylic acids from the corresponding α-hydroxynitriles, and specifically, to the preparation of these compounds via reactions catalyzed by microbial enzymes. The invention particularly relates, in a preferred embodiment, to the enzymatic conversion of 2-hydroxy-4-(methylthio)-butanenitrile to 2-hydroxy-4-(methylthio)-butaneamide, 2-hydroxy-4-(methylthio)-butanoic acid or salts thereof.

Traditionally, α-hydroxyamides have been prepared by hydrating the corresponding nitrile under very acidic conditions, and α-hydroxy acids have been prepared by acid hydrolysis of the corresponding nitrile through an α-hydroxyamide intermediate. Salts of α-hydroxy acids, including metal salts such as calcium salts, have been prepared from the α-hydroxy acid by contacting the acid with metal oxides, hydroxides or carbonates.

More recently, biological processes for preparing α-hydroxyamides and α-hydroxyacids have been developed. The processes disclosed in U.S. Pat. No. 4,001,081 to Commeyras et al., in Japanese Patent Applications 4-40898 and 4-40899 and in PCT Application WO 96/09403 A1 are exemplary. However, the enzymatic conversion of α-hydroxynitriles to the corresponding amides and acids is reported as being inhibited at higher concentrations of nitrile substrate. European Patent Publication No. 0666320A2 reports that the observed nitrile inhibition is due to dissociation of the α-hydroxynitrile into its corresponding aldehyde, and suggests the use of phosphite or hypophosphite ions to complex with the aldehyde and prevent inhibition of the enzyme. Despite such suggestions, the reported processes have not been successful in enzymatically converting α-hydroxynitriles to the corresponding amides or acids at significant yields and at concentrations sufficiently high to be commercially attractive.

SUMMARY OF THE INVENTION

It is therefore an object of the present invention to effect enzymatic hydration of an α-hydroxynitrile to the corresponding amide at product concentrations suitable for commercial production thereof. It is likewise an object to reduce the extent of nitrile inhibition during enzymatic conversion to the amide or acid and to effect such conversions at relatively high yields.

Briefly, therefore, one aspect of the present invention is directed to processes for the enzymatic conversion of a substituted or unsubstituted α-substituted-butyronitrile to a corresponding α-substituted-butyramide. In a preferred process the α-substituted-butyronitrile is an α-hydroxybutyronitrile such as 2-hydroxy-4-(methylthio)-butanenitrile. However, other α-substituted-butyronitriles (e.g. α-amino-butyronitriles such as 2-amino-4-(methylthio)-butanenitrile) could also be used in the process of the present invention. One preferred process comprises hydrating the α-hydroxybutyronitrile in the presence of a microbial enzyme to form the corresponding α-hydroxybutyramide. The enzyme has the capability of hydrating the α-hydroxybutyronitrile in a solution (e.g. an aqueous solution) saturated with the α-hydroxy-butyramide. Another preferred process comprises hydrating the α-hydroxybutyronitrile in the presence of microbial cells or cell lysates to form the corresponding α-hydroxybutyramide. The cells or cell lysate have the capability of hydrating the α-hydroxybutyronitrile in a solution saturated with the α-hydroxybutyramide. In a further preferred process, 2-hydroxy-4-(methylthio)-butanenitrile is enzymatically hydrated in an aqueous reaction solution to form 2-hydroxy-4-(methylthio)-butaneamide. The resulting product, 2-hydroxy-4-(methylthio)-butaneamide, is present in the reaction solution during at least a portion of the reaction at a concentration ranging from about 50% to 100% of its saturation concentration. In the aforementioned preferred process, an aqueous cell suspension comprising whole cells of strains 52 or 56 wt is prepared or obtained. These cell strains are deposited with the American Type Culture Collection, Accession No. 55923 and No. 55924, respectively. 2-Hydroxy-4-(methylthio)-butanenitrile having less than about 0.5 mole % hydrogen cyanide present therein relative to the amount of 2-hydroxy-4-(methylthio)-butanenitrile is likewise obtained or prepared. The cell suspension is then combined with 2-hydroxy-4-(methylthio)-butanenitrile to form a reaction solution. The concentration of 2-hydroxy-4-(methylthio)-butanenitrile in the reaction solution is maintained at less than about 100 mM and the temperature of the reaction solution ranges from about 2° C. to about 30° C.

The invention is also directed to the enzymatic conversion of an α-hydroxynitrile to a corresponding α-hydroxyamide. In this process, α-hydroxynitrile having less than about 0.5 mole % hydrogen cyanide present therein relative to the amount of α-hydroxynitrile is prepared or obtained, and enzymatically hydrated to form an α-hydroxyamide.

The invention is directed, as well, to a process for the enzymatic conversion of a nitrile to a corresponding amide. The nitrile is hydrated in the presence of a microbial enzyme to form the corresponding amide. The enzyme is derived or obtained from microbial strains 52 or 56 wt deposited with the American Type Culture Collection, Accession No. 55923 and No. 55924, respectively. Preferred nitriles in this process include, for example, α-hydroxynitriles, butyronitriles, α-substituted-butyronitriles, α-hydroxybutyronitriles and 2-hydroxy-4-(methylthio)-butanenitrile.

The invention is directed, moreover, to a process for the enzymatic conversion of an amide to a corresponding carboxylic acid. The amide is hydrolyzed in the presence of a microbial enzyme to form the corresponding carboxylic acid. The enzyme is derived or obtained from strains 52 or 56 wt deposited with the American Type Culture Collection, Accession No. 55923 and No. 55924, respectively. Preferred amides include hydroxyamides, butyramides, α-substituted-butyramides, α-hydroxybutyramides and 2-hydroxy-4-(methylthio)-butaneamide.

Yet another aspect of the invention is directed to the enzymatic conversion of a nitrile to a corresponding carboxylic acid. The nitrile is hydrated to form a corresponding amide, and the amide is hydrolyzed to form the corresponding carboxylic acid. The hydration reaction and/or the hydrolysis reaction are carried out in the presence of a microbial enzyme derived from strains 52 or 56 wt deposited with the American Type Culture Collection, Accession No. 55923 and No. 55924, respectively. Preferred nitriles in this process include, for example, α-hydroxynitriles, butyronitriles, α-substituted-butyronitriles, α-hydroxybutyronitriles and 2-hydroxy-4-(methylthio)-butanenitrile.

A further aspect of the present invention is directed to a process for the preparation of salts of 2-hydroxy-4-

(methylthio)-butanoic acid from 2-hydroxy-4-(methylthio)-butanenitrile. 2-Hydroxy-4-(methylthio)-butanenitrile is enzymatically hydrated to form 2-hydroxy-4-(methylthio)-butaneamide, and the resulting 2-hydroxy-4-(methylthio)-butaneamide is hydrolyzed in a basic solution to form a salt of 2-hydroxy-4-(methylthio)-butanoic acid.

The invention is directed, in another aspect, to isolated and substantially purified microorganisms. One microorganism of the invention is designated herein as strain 52 and deposited with the American Type Culture Collection, Accession No. 55923. Another microorganism of the invention is designated herein as strain 56 wt and deposited with the American Type Culture Collection, Accession No. 55924.

Other features and objects of the present invention will be in part apparent to those skilled in the art and in part pointed out hereinafter.

BRIEF DESCRIPTION OF THE DRAWINGS

FIG. 1A shows resulting peaks A, B, C and D corresponding to dodecane (an internal standard) (A), HMB-nitrile (B), HMB-acid (C) and HMB-amide (D) after 2 hours of reaction. FIG. 1B shows peaks corresponding to dodecane (A) and HMB-acid (C) after 8 hours of reaction. The large unlabeled peaks in FIGS. 1A and 1B correspond to ethyl acetate solvent and derivatizing agent.

FIG. 3 is a graph showing the initial reaction rate versus the initial concentration of 2-hydroxy-4-(methylthio)-butanenitrile (HMB-nitrile) substrate for the conversion of untreated HMB-nitrile to the corresponding amide in the presence of enzymes derived from microbial strain 52.

FIG. 4 is a graph showing the early reaction progress for the bioconversion of untreated 2-hydroxy-4-(methylthio)-butanenitrile (HMB-nitrile) to HMB-amide using strain 52 whole cells which were pre-incubated in a solution consisting of untreated HMB-nitrile (100 mM) in 0.1M $Na_2HPO_4$/$KH_2PO_4$ buffer, pH 7.1, for various lengths of time prior to being used in the hydration reaction. As a control, strain 52 whole cells were incubated in buffer, but without HMB-nitrile, prior to use in an equivalent hydrolysis reaction.

FIGS. 5A and 5B are graphs showing the early reaction progress for the bioconversion of untreated 2-hydroxy-4-(methylthio)-butanenitrile (HMB-nitrile) to HMB-amide using strain 52 whole cells where the HMB-nitrile substrate was hydrated: (1) using whole-cell catalyst in the presence of potassium cyanide at various concentrations (FIG. 5A); and (2) using whole-cell catalyst which had been preincubated with potassium cyanide at various concentrations for one hour prior to carrying out the reaction (FIG. 5B).

FIGS. 7A and 7B are graphs showing data related to the bioconversion of untreated 2-hydroxy-4-(methylthio)-butanenitrile (HMB-nitrile) to HMB-amide using strain 52 whole cells in the presence of various initial concentrations of HMB-amide (0 mM, 100 mM, 250 mM, 500 mM, 750 mM, 1000 mM, 1250 mM and 1500 mM). FIG. 7A shows the concentration of HMB-nitrile remaining at various times during the reaction, and FIG. 7B shows the corresponding initial reaction rates.

FIGS. 9A and 9B are graphs showing the early reaction progress for the bioconversion of untreated 2-hydroxy-4-(methylthio)-butanenitrile (HMB-nitrile) to HMB-amide using strain 52 whole cells which were preincubated for various times in either buffer solution (0.1M $Na_2HPO_4$/$KH_2PO_4$ buffer, pH 7.1) or in 100 mM nitrogen-purged HMB-nitrile. The reactions were carried out at a temperature of either 22° C. (FIG. 9A) or, in separate runs, 2.5° C. (FIG. 9B).

Figure 1A:
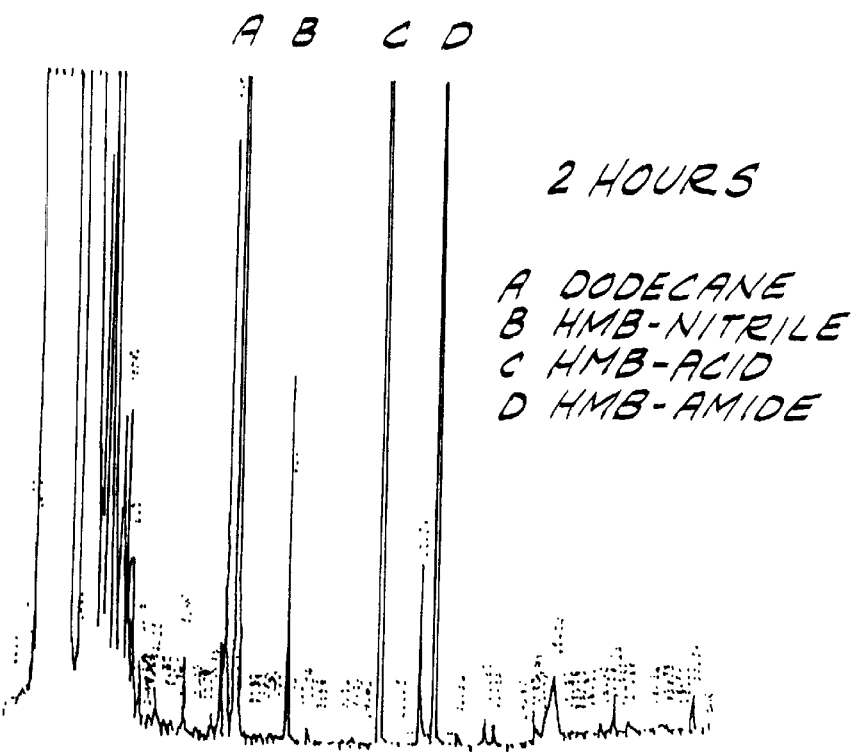
FIGS. 1A and 1B are gas chromatograms of reaction samples taken during the enzymatic conversion of 2-hydroxy-4-(methylthio)-butanenitrile (HMB-nitrile) and 2-hydroxy-4-(methylthio)-butaneamide (HMB-amide) to the corresponding amide and acid, respectively, using enzymes derived from whole cells of strains 52.

The invention is described in further detail below with reference to the figures.

DETAILED DESCRIPTION OF THE INVENTION

Enzymes derived from the isolated and substantially purified microorganisms of the present invention, designated herein as strains 52 and 56 wt, have the ability to hydrate α-hydroxynitriles to the corresponding amide, and further, to hydrolyze α-hydroxyamides to the corresponding carboxylic acid. (Example 1). While the nitrile→amide reaction is referred to in some references in the art as being a "hydrolysis" rather than a "hydration" reaction, the terms "hydrate", "hydration" and the like are, as used herein, intended to describe a reaction whereby an organic-cyanide molecule is converted to its corresponding amide by the addition of $H_2O$. The term "hydrolysis", as used herein, is intended to refer to a reaction in which an amide is converted to its corresponding acid or acid salt. The terms "enzyme" and "enzymes" are intended to be used interchangeably, with both terms including the singular and the plural, and including, for example, multiple enzymes having a particular activity and/or a single enzyme having one or more activities. An "isolated and substantially purified" microorganism means a microorganism such as a bacterial cell which is present outside its naturally occurring environment and is present at a concentration which is greater than its concentration in a naturally occurring environment. Nitrile hydratases and/or amidases are considered to be "derived from" microbial cells such as strains 52 or 56 wt if the enzymes originate directly or indirectly from the cells, including for example: being expressed in microbial whole cells; being present in the cytosol thereof; being present in a cell culture thereof; being present in a cell lysate thereof; being isolated, sequenced and synthetically prepared; and/or being obtained using recombinant DNA technology, such as from a genetically engineered plasmid / host cell system in which the plasmid includes a nucleic acid polymer (e.g. cDNA) which encodes the nitrile hydratase and/or the amidase enzymes. Without being bound by theory, the enzymatic conversion of the α-hydroxynitrile to the corresponding acid is believed to occur via a two-step (nitrile hydratase, amidase) protocol, rather than as a single step (nitrilase) conversion. (Example 1). Neither the nitrile hydratase or the amidase are enantiomerically specific with regard to their respective substrates.

Advantageously, the catalytic action of the nitrile hydratases of strains 52 and 56 wt is not substantially inhibited by the α-hydroxyamide product being formed; rather, these enzymes are capable of hydrating an α-hydroxybutyronitrile in a solution saturated with the corresponding amide product. As such, enzymes derived from strains 52 and 56 wt are particularly suited for commercial use in preparing α-hydroxybutyramides such as 2-hydroxy-4-(methylthio)-butaneamide at relatively high concentrations thereof. The α-hydroxyamides prepared using such enzymes may be hydrolyzed, through traditional or enzymatic conversion methods, to form corresponding acids or acid salts. The conversion of α-hydroxynitriles to the corresponding amides, acids or acid salts is industrially important for the preparation of various pharmaceuticals and agrichemicals. In particular, 2-hydroxy-4-(methylthio)-butanoic acid and salts thereof, produced by the methods disclosed herein from 2-hydroxy-4-(methylthio)-butanenitrile via the corresponding amide, are useful as methionine substitutes in feeds for domestic animals such as chickens.

Strains 52 and 56 wt were isolated from natural soil samples based on the ability to use various nitriles as principle nutrient sources of nitrogen and/or carbon. (Example 2). Strains 52 and 56 wt are gram positive, rod-shaped bacteria which, based on microbial identification assays, belong to the genus Rhodococcus. (Example 2). Microbial strains 52 and 56 wt were deposited on Jan. 10, 1997 with the American Type Culture Collection (ATCC, Rockville, Md.) under Accession No. 55923 and Accession No. 55924, respectively.

Strains 52 or 56 wt cells may be grown in a fermentation reactor by aerobically culturing the cells in media which provide an adequate supply of carbon, nitrogen, and necessary nutrients. The culture medium can include a carbon source (e.g. glucose, maltose, succinate, whey, etc.), a nitrogen source (e.g. ammonium chloride, ammonium sulfate, etc.), an organic nutrient source (e.g. yeast extract, malt extract, corn-steep liquor, peptone, meat extract, etc.) and an inorganic nutrient source (e.g. phosphate, magnesium, potassium, zinc, iron, manganese, etc.). Nitriles (e.g. acetonitrile, benzonitrile and butyronitrile) may be used as a supplemental nitrogen source in liquid culture media. A preferred culture medium for growth of these strains includes succinate (supplied as 5 g/l succinic acid neutralized with NaOH to pH 7.1), yeast extract (1 g/l), $MgSO_4$ (160 mg/l), $FeSO_4$, (8 mg/l), $MnSO_4 \cdot H_2O$ (3 mg/l) $CoSO_4 \cdot 7H_2O$ (3 mg/l) and $ZnSO_4 \cdot 7H_2O$ (3 mg/l) in a $Na_2HPO_4/KH_2PO_4$ buffer (50 mM, pH 7.1). Growth may be carried out under aerobic conditions while maintaining the pH of the culture medium at a pH of about 7.1. The temperature of the growth medium can be about 28° C. The time required for culturing the cells will depend on the particular medium and conditions, but cell suspensions having a concentration of about 0.5 g/l–1 g/l on a dry weight basis can be grown in about one day in the aforementioned culture system. Microbial strains 52 and 56 wt may alternatively be grown in solid culture medium using nitriles (e.g. acetonitrile, benzonitrile and butyronitrile) as the sole nitrogen source.

During culturing, strain 52 or 56 wt cells are preferably exposed to one or more inducers which facilitate expression of the biocatalytic enzymes and/or to one or more activity enhancers, which enhance the nitrile hydratase and/or amidase activities of the enzymes. Inducers and/or enhancers are preferably added directly to the growth medium, such that the cells are cultured in an inducer-enriched and enhancer-enriched medium. The cells can also be exposed to a volatile inducer/enhancer present in the atmosphere over the growth medium. Nitriles such as butyronitrile or ε-caprolactam are exemplary inducers, with butyronitrile being a preferred inducer. Cobalt is an exemplary activity enhancer. The concentration of the inducer and/or activity enhancers in the growth medium may affect the nitrile hydratase and/or amidase activity of the cells. For the enzymatic conversion of 2-hydroxy-4-(methylthio)-butanenitrile, strain 52 and 56 wt cells may be cultured in a growth medium which includes butyronitrile (0.2% by weight per volume, e.g. 0.2 g per 100 ml) and/or cobalt (about 5 mM to about 15 mM). (Example 3).

Cell growth can be carried out as a batch process or as a continuous process. Batch processes for growing cells of strains 52 or 56 wt are suitable where subsequent hydration and/or hydrolysis reactions will be carried out as batch processes or where it is desired to intermittently prepare a supplemental cell suspension to augment a cell population already in use in either a batch or continuous reaction scheme. Continuous processes for cell growth may be suitably used where the subsequent enzymatically catalyzed reactions are carried out as continuous processes. Where the hydration and/or hydrolysis reactions occur in a different vessel than the vessel in which the cells were grown, or where these reactions occur at a later time, the biomass may be harvested, preferably washed free of any inducing nitriles and, if necessary, stored for later use. Whole cells may be harvested and stored for short durations in a cell suspension. For longer durations, the cells may be stored by freezing. (Example 4). Alternatively, the cells could be stored as dried cells.

The nitrile hydratase and/or amidase enzymes derived from strains 52 or 56 wt can be supplied to the reaction zone of a suitable reactor as a suspension of freely circulating whole cells, as a cell lysate or as immobilized cells. (Example 5). An aqueous cell suspension comprising whole cells of strains 52 or 56 wt may be prepared by culturing cells as described above, harvesting the cells (e.g. by centrifuging, sedimentation, settling, filtering, etc.), washing with a buffer solution (e.g. $Na_2HPO_4/KH_2PO_4$ buffer, 50 mM, pH 7.1), and resuspending the cells in a buffer solution at the desired cell concentration. When the enzymes are supplied to the reaction in the form of whole cells, some of the cells may spontaneously lyse during the reaction. Lysates of the whole cells may also be used in the reaction without a significant difference in nitrile hydratase activity. Such cell-free extracts can be prepared, for example, by passing cultured cells through a press or extruder and then clearing the lysate of cell debris by centrifuging, filtration, etc. Alternatively, the cells may be used in the reaction in immobilized or conjugated form, while still retaining enzymatic activity. For example, the cells may be crosslinked to each other with a bi-functional cross-linking agent, conjugated to a polymer or other macromolecule, and/or bonded either directly or through a linking molecule to a suitable matrix or solid support substrate. The conjugating moiety and/or the substrate to which the cells are linked is preferably biologically inert with respect to the enzymatic activity of the cells and chemically inert with respect to the reaction solution.

Nitrile substrates such as α-hydroxynitriles may be obtained from commercial sources and/or by methods known in the art. 2-Hydroxy-4-(methylthio)-butanenitrile can be prepared, for example, by reacting commercially available acrolein with methyl mercaptan to form 3-(methylthio)-propanal (MMP) and reacting MMP with hydrogen cyanide.

An α-hydroxynitrile is enzymatically converted to its corresponding amide by supplying both the nitrile substrate and the enzymes derived from strains 52 and 56 wt to a reaction medium. The reaction medium is preferably an aqueous solution and most preferably a buffered aqueous solution. The reaction medium could, however, be a non-aqueous solution such as an alcohol (e.g. methanol) provided that such solution has at least a stoichiometric amount of water to effect the hydration and/or hydrolysis reactions as desired. The hydration of the α-hydroxynitrile is catalyzed by the nitrile hydratase activity of the strain 52 and 56 wt cells. For the enzymatic conversion of 2-hydroxy-4-(methylthio)-butanenitrile (HMB-nitrile) to its corresponding amide, the nitrile hydratase is reasonably active in aqueous solutions having HMB-nitrile concentrations of about 100 mM, but less active in such solutions having HMB-nitrile concentrations of about 200 mM. (Example 6). The observed substrate inhibition appears to be at least partially caused by the presence of free hydrogen cyanide in the nitrile feed liquid (typically ranging from about 0.25% to 1% by weight—about 1% to about 5% by mole—relative to nitrile). While some lesser amount of the corresponding aldehyde is also typically present in the nitrile feed, the hydrogen cyanide is the more significant inhibiting contributor; the aldehyde has little, if any, inhibiting effect. (Example 7).

As such, the α-hydroxynitrile substrate and/or a solution comprising the substrate is preferably treated to reduce the amount of hydrogen cyanide present during the reaction, thereby minimizing the degree of cyanide inhibition of the nitrile hydratase activity. The α-hydroxynitrile (or a solution comprising the nitrile substrate) can be pretreated to remove hydrogen cyanide, for example, by contacting the nitrile (or nitrile solution) with a stripping gas. The stripping gas is preferably an inert gas such as nitrogen. However, other gases, including mixed gases such as air can also be used to strip hydrogen cyanide from the liquid nitrile. The nitrile temperature, stripping gas pressure, stripping gas flow rate and time of stripping are not narrowly critical, but should generally be controlled so as to effectively reduce the concentration of hydrogen cyanide in the nitrile feed. For example, a nitrile feed sample of about 110 g (4 oz.) can be sparged using nitrogen at atmospheric pressure, at room temperature and at a gas flow rate of about 15 cc/min for about 4 to 6 hours. The extent of subsequent decomposition of the nitrile to hydrogen cyanide and its corresponding aldehyde is preferably minimized by hydrating the pretreated nitrile as soon as practical and preferably within about 24 hours after the stripping of hydrogen cyanide is completed and most preferably within about 12 hours thereof. However, the pretreated nitrile can be stored for significantly longer periods without the formation of substantial amounts of hydrogen cyanide by storing under refrigeration (e.g. 4° C.) or frozen (e.g. −20° C.). Hydrogen cyanide is preferably stripped from the nitrile substrate (or nitrile solution) before the substrate is fed to the reaction zone and before the reaction occurs. Alternatively or additionally, the reaction solution can be contacted with a stripping gas during the hydration reaction to maintain the level of hydrogen cyanide sufficiently low to substantially avoid cyanide inhibition. Other possible methods for reducing the amount of hydrogen cyanide present in the reaction medium include pretreatment of the nitrile or a nitrile solution with one or more cyanide-degrading enzymes, such as those described in Kunz et al., Alternative Routes of Enzymic Cyanide Metabolism in Pseudomonas fluorescens NCIMB11764, Microbiology, Vol. 140, pp.1705–1712 (1994) or in Dubey and Holmes, Biological Cyanide Destruction Mediated by Microorganisms, World Journal of Microbiology and Biotechnology, Vol. 11, pp.257–265 (1995). Additionally or alternatively, such cyanide-degrading enzymes could be added to the reaction mixture to degrade cyanide during the hydration and/or hydrolysis reaction. Regardless of the method used, the hydrogen cyanide concentration present in the α-hydroxynitrile being fed to the reactor or in a feed solution containing the nitrile is preferably equal to or less than about 0.5 mole % (about 1000 ppm by weight) relative to the amount of α-hydroxynitrile, more preferably equal to or less than about 0.25 mole %, even more preferably equal to or less than about 0.1 mole % and most preferably equal to or less than about 0.05 mole % relative to the amount of α-hydroxynitrile. The amount of hydrogen cyanide present in the reaction zone during the reaction is also preferably less than the above recited amounts.

In addition to minimizing the presence of hydrogen cyanide in the nitrile feed and in the reaction solution, other methods directed toward reducing nitrile hydratase inhibition may also be used where appropriate. For example, while the aldehyde present in the reaction system in which the nitrile substrate was 2-hydroxy-4-methylthiobutanenitrile was determined to have little, if any, inhibiting effect on nitrile hydratase activity of strains 52 and 56 wt, aldehydes present in reaction systems with other nitrile substrates may have a more appreciable inhibiting effect. In such a case, aldehyde inhibition can also be reduced, for example, by complexing the aldehyde with phosphite or with other complexing agents.

Although the hydration reaction is, as discussed above, inhibited by high concentrations of the nitrile substrate, the nitrile hydratase activity is substantially less inhibited by the amide product formed. Advantageously, the enzymes derived from strains 52 and 56 wt are capable of hydrating an α-hydroxybutyronitrile in a reaction solution having a high amide concentration, including in a reaction solution saturated with the product amide (Example 8). Saturation concentrations will generally depend on temperature, pH and solution composition (e.g. the particular α-hydroxyamide product formed, the solvent system used, the amount of unreacted nitrile remaining and the amount of acid formed). Saturation concentrations for 2-hydroxy-4-(methylthio)-butaneamide (HMB-amide) in an aqueous $Na_2HPO_4/KH_2PO_4$ buffer solution (50 mM, pH 7.1) are about 1M at 30° C. and about 600 mM at 6° C. For conversion of HMB-nitrile to HMB-amide at 28° C. in a reaction solution saturated with HMB-amide, the nitrile hydratase has an average specific activity of at least about 20 $\mu$mole·min$^{-1}$/g dry cells, more preferably at least about 50 $\mu$mole·min$^{-1}$/g dry cells, even more preferably at least about 100 μmole·min$^{-1}$/g dry cells, and most preferably at least about 200 μmole·min$^{-1}$/g dry cells as measured over a period of about 1 hour. The specific activity in a reaction solution at 6.5° C. saturated with HMB-amide is preferably at least about 30 μmole·min$^{-1}$/g dry cells, more preferably at least about 50 μmole·min$^{-1}$/g dry cells and even more preferably at least about 100 μmole·min$^{-1}$/g dry cells averaged over a period of about 12 hours.

The capability of the strain 52 and 56 wt enzymes to hydrate α-hydroxynitriles in solutions having a high concentration of amide can be employed advantageously. While the particular reaction configuration will vary depending on whether the enzymatic conversion is carried out as a batch, semicontinuous or continuous process, the reaction generally can be carried out with the concentration of amide present in the reaction solution being greater than about 50% of the amide saturation concentration, greater than about 75% of its saturation concentration, greater than about 90% of its saturation concentration or greater than about 95% of its saturation concentration. The reaction can also be carried out at saturated amide concentration (100% saturated solution) with the formation of amide crystals in the reaction solution. For the preparation of 2-hydroxy-4-(methylthio)-butaneamide by enzymatic hydration of 2-hydroxy-4-(methylthio)-butanenitrile, the concentration of the amide in the reaction solution can be, in general, greater than about 300 mM, greater than about 400 mM, and greater than about 500 mM. At a temperature of about 6° C., the concentration of HMB-amide in the reaction solution can range from about 300 mM to about 600 mM. At a temperature of about 30° C., the concentration of HMB-amide can range from about 500 mM to about 1M. Operation at saturated or near-saturated amide conditions, whether during the latter stages of a batch process or at steady state during a continuous process, can result in a reaction mixture saturated with amide and containing undissolved amide crystals. Redissolving the amide crystals results in a higher concentration of amide. (Example 13). As discussed below, high amide concentrations in the reaction solution inhibit the amidase activities of strains 52 and 56 wt and therefore limit the extent of α-hydroxy acid formation via the further hydrolysis reaction. To minimize α-hydroxy acid formation, the amide concentration is preferably at least about 400 mM at a temperature of 28° C. (Example 8). However, because the benefits of operating at higher amide concentrations are offset somewhat by a slightly lower nitrile hydratase activity, the optimal concentration of amide in the reaction medium will vary with a particular reactor design, reaction kinetics, downstream separation process or processes, variations in energy requirements, and the associated economics of a given application, alone, or in combination with other production concerns. The optimal amide concentration of the reaction solution during the latter stages of a batch process or at steady state during a continuous process, based on overall economic considerations, may be less than the saturated amide concentration, but will generally be equal to or greater than about 50% of the saturated amide concentration.

Nitrile hydratase activity is also relatively independent of the presence of carboxylic acid (amidase product) or salts thereof. The nitrile hydratases remained active even at about 1M concentrations of the corresponding carboxylic acid ammonium salt. (Example 9). Hence, the formation of a relatively small amount of α-hydroxy carboxylic acid as a by-product will not inhibit the nitrile hydration reaction. Nonetheless, the α-hydroxyamide is preferably prepared in a manner which minimizes the amount of the corresponding acid which forms as a by-product, in order to maximize amide yield and minimize subsequent separation efforts and costs. For the enzymatically catalyzed production of 2-hydroxy-4-(methylthio)-butaneamide from the corresponding nitrile, the amount of 2-hydroxy-4-(methylthio)-butanoic acid formed is preferably less than about 5% relative to the amount of HMB-nitrile substrate fed or added to the reaction zone and more preferably less than about 1% relative to the amount of HMB-nitrile substrate added.

According to a preferred method for producing an α-hydroxyamide, the enzymes are supplied to a reaction zone of a reactor as a buffered aqueous suspension of whole cells. α-Hydroxynitrile is preferably pretreated (e.g., $N_2$ sparged) to decrease the amount of hydrogen cyanide present therein, and then combined directly or as a buffered aqueous solution with the whole-cell suspension to form an aqueous reaction solution in which the nitrile is enzymatically hydrated. The buffered solution used to suspend the whole cells can be used as the reaction solvent. While the exact concentration of cells in the reaction solution is not narrowly critical, the nitrile hydratase activity generally increases with increasing cell concentration. (Example 10). For the conversion of 2-hydroxy-4-(methylthio)-butanenitrile to its corresponding amide, a cell suspension having a concentration ranging from about 1 g/l (dry weight) to about 100 g/l (dry weight) before the addition of nitrile can be used, with a concentration of about 80 g/l (dry weight) being preferred. After addition of the nitrile to the reaction solution, the concentration of whole cells in the reaction solution preferably ranges from about 25 g/l (dry weight) to about 40 g/l (dry weight). The concentration of nitrile in the reaction solution is preferably maintained at less than about 200 mM, more preferably at less than about 100 mM and most preferably at about or less than about 50 mM. Real-time monitoring of the nitrile concentration (e.g. by HPLC assays as described below) may be used to facilitate resupply of nitrile substrate to the reaction solution as the reaction progresses. Such substrate resupply could be accomplished by continuous or progressive feed throughout a batch cycle or during a continuous production run. Supplementary amounts of the cell suspension may also be added to the reaction solution as the reaction progresses. Control of the rate of addition of supplemental cells can be facilitated by monitoring the progress of the reaction, with additional cells being added as the reaction rate slows.

The temperature of the reaction solution is preferably maintained from about 2° C. to about 30° C. during the reaction. (Examples 11 and 12). Lower temperatures (e.g. from about 2° C. to about 10° C.) are preferred to the improve the stability of the nitrile hydratase activity (Example 12). Temperatures ranging from about 2° C. to about 7° C. are most preferred with respect to catalyst stability. Lower temperatures also result in relatively decreased conversion of the resulting HMB-amide product to HMB-acid (via hydrolysis reaction) as compared to reactions at higher temperatures. While lower temperatures favor catalyst stability and minimize hydrolysis of HMB-amide, higher temperatures (e.g. from about 10° C. to about 25° C.) are preferred to improve the reaction kinetics and to effect the conversion under practical industrial conditions. Accordingly, optimal reaction temperature will vary in light of such considerations. While the hydration reaction is exothermic in nature, temperature control may not be narrowly critical for dilute reaction solutions. However, the reaction temperature can, if necessary, be controlled by suitable heat removal means.

The reaction pressure is not narrowly critical and the reaction can be conducted at atmospheric pressure. The pH of the reaction solution is preferably about 7.1. The reaction solution is preferably well mixed or agitated throughout the reaction. Positive aeration of the reaction mixture and/or cell viability in the reaction solution is not narrowly critical for maintaining enzyme activity during the reaction. However, aeration during the reaction may be accomplished, if desired, by employing an aerobic fermentation reactor. While the time for effecting the conversion reaction will vary depending on the various possible reaction conditions, reaction solutions having high concentration (e.g. >50 mole % of the amide saturation concentration) can be realized in about 10 to 30 hours for a batch conversion effected at temperature ranging from about 2.5° C. to about 6.5° C. In a preferred reaction, 2-hydroxy-4-(methylthio)-butaneamide (HMB-amide) is produced by supplying nitrogen-sparged HMB-nitrile at a concentration of about or less than about 50 mM to a bioreactor supplied with an aqueous whole-cell suspension of strain 52 or strain 56 wt cells and at a reaction temperature of about 6.5° C. (Example 13).

The enzymatic conversion of an α-hydroxynitrile to its corresponding amide and/or acid can be carried out in batch, semicontinuous or continuous mode. The reactor type and particular design may vary depending on operational considerations, but reactors such as a fermentation reactor or a stirred tank reactor (batch or continuous) are suitable. Regardless of the reactor type or design, the reactor can generally include: inlet ports for admitting substrate, catalyst (enzyme) and additional nutrients and/or activity enhancers; outlet ports for discharging a product stream; means for mixing or agitating (e.g. motor driven impeller); means for aerating (e.g. spargers) including gas inlets and vents; control elements and systems for controlling temperature (e.g. heaters, cooling jackets), pH (e.g. acid base reservoir w/pH controller), level, etc.; and means for real-time monitoring and control of substrate, catalyst and/or product concentration. A batch process can be carried out in one or more reactors by growing cells in a fermentation reactor as described above and, if desired, harvesting, washing, and resuspending the cells at the desired cell concentration. The cell suspension can be returned to either the fermentation reactor in which they were grown or to a second fermentation reactor or a stirred tank reactor. The nitrile substrate is added to the reactor containing the cell suspension and the nitrile is enzymatically hydrated in a reaction solution to the desired amide as described above. After the reaction is complete, the resulting product mixture can be discharged from the hydrating reactor for separation and isolation of the desired amide. In a semicontinuous process, fresh cells are cultured in a fermentation reactor while the hydration reaction is carried out in a second reactor. Supplemental cells can be intermittently added to the reaction solution as necessary to ensure sufficient enzymatic activity. Likewise, the initial concentration of nitrile substrate can be relatively low to minimize nitrile inhibition of the hydration reaction and supplemental nitrile substrate can be intermittently added as needed. After the reaction is complete, the resulting product mixture can be discharged from the hydrating reactor for separation and isolation of the desired amide. In a continuous process, the cells can be continuously cultured and harvested from a continuous fermentation reactor. After washing and resuspending the cells at the requisite concentration, a cell suspension can be continuously and/or intermittently supplied to a continuous stirred tank reactor (CSTR). Nitrogen-sparged α-hydroxynitrile substrate is progressively fed and/or continuously added to the CSTR and enzymatically hydrated. As noted, the concentration of product amide in the reaction solution will preferably range from about 50% to 100% of its saturation concentration, as dictated by the overall concerns of maximizing productivity and minimizing costs. A product stream comprising a product mixture is continuously discharged from the CSTR and, as discussed below, the desired amide and the cells are separated from the product mixture. In some applications, it may be desirable to recycle cells separated from the product discharge stream to the CSTR to augment the supply of freshly grown cells supplied from the fermentation reactor.

The product mixture resulting from the hydration reaction (whether carried out by batch, semicontinuous or continuous processes), can generally include the α-hydroxyamide, residual unreacted nitrile substrate, α-hydroxy carboxylic acid, buffer salts, whole cells and cell debris from spontaneously lysed cells in the buffer solution used in creating the cell suspension. In batch operations in which 2-hydroxy-4-(methylthio)-butanenitrile (HMB-nitrile) is hydrated to HMB-amide, more than about 99% of the HMB-nitrile substrate can be converted, with the HMB-amide being the predominant conversion product. Specifically, at least about 90 mole % of the HMB-nitrile substrate in the reaction solution is converted to amide, less than 5 mole % of the HMB-nitrile is converted to acid and less than 1 mole % of the HMB-nitrile remains unreacted. When HMB-nitrile is hydrated at temperatures of less than about 7° C., the concentration of HMB-acid produced from the desired HMB-amide product via the amidase reaction is less than about 50 mM.

The desired α-hydroxyamide can be separated from the product mixture by a variety of possible separation and isolation schemes. For example, amide crystals which developed during the reaction may be redissolved by heating the product mixture. For dissolution of 2-hydroxy-4-(methylthio)-butaneamide crystals, the reaction solution can be heated to a temperature of about 50° C. The cells and cell debris may then be removed from the heated product mixture by centrifugation, sedimentation, settling and/or filtering processes. The desired α-hydroxyamide may be recovered from the cell-free product mixture (ie, from the supernatant, sedimentation liquor, filtrate, etc) by recrystallizing the amide. 2-Hydroxy-4-(methylthio)-butaneamide can be recrystallized by cooling the cell-free product mixture to about 4° C. If desired, additional washings (dissolutions/recystallizations) can be carried out. In an alternative separation scheme, where the cells will be recycled, they are preferably separated from the product mixture in a manner and at a time which maximizes the enzymatic activity of the cells. The aforementioned reaction/separation schemes are to be considered exemplary and non-limiting, as variations and modifications and completely new schemes will be apparent to those of skill in the art.

Strains 52 and 56 wt can be also used to effect the enzymatic conversion of an amide, such as 2-hydroxy-4-(methylthio)-butaneamide (HMB-amide), to its corresponding carboxylic acid. However, the amidase activity of the enzymes derived from strains 52 and 56 wt is sensitive to modest concentrations of α-hydroxy carboxylic acid (product), amide (substrate) and/or nitrile (nitrile hydratase substrate). For the enzymatic conversion of 2-hydroxy-4-(methylthio)-butaneamide (HMB-amide) to HMB-acid using strains 52 or 56 wt, the amidase is inhibited by the presence of HMB-nitrile at concentrations above about 200 mM (Example 6), by HMB-amide substrate above about 400 mM (Example 8) and by HMB-acid product above about 200 mM (Example 9). Accordingly, the amidase reaction is preferably carried out under conditions which minimize the inhibitory effect of these compounds.

The corresponding acid can, alternatively, be prepared from the enzymatically-prepared α-hydroxyamide using conventional chemical means, including for example, acid hydrolysis, or via either the corresponding ester or salt intermediates. Moreover, salts and other derivatives of α-hydroxy acids such as 2-hydroxy-4-(methylthio)-butanoic acid (HMB-acid) can be prepared from the α-hydroxyamide obtained by enzymatic conversion of α-hydroxynitrile. For example, HMB-nitrile can be hydrated in the presence of a microbial enzyme (e.g. enzymes derived from strains 52 or 56 wt) to form HMB-amide as described above. The HMB-amide may then be used in a variety of further processes known in the art, including for example, a number of reactions using amide substrate described generally in U.S. Pat. No. 2,745,745 to Blake et al., the preparation of a corresponding alkyl ester using an alkyl formate reagent as described in EP 0601195 A1, and the preparation of a corresponding salt via a basic hydrolysis mechanism as described in EP 0731079 A2.

In a preferred use, the enzymatically prepared HMB-amide is hydrolyzed in basic solution and most preferably a basic aqueous solution to form an HMB-acid salt. For example, the calcium salt can be prepared by hydrolyzing the enzymatically prepared HMB-amide in the presence of calcium oxide, calcium hydroxide or calcium carbonate. The sodium salt can be prepared by hydrolyzing the HMB-amide in the presence of sodium hydroxide. The zinc salt can be prepared by hydrolyzing the HMB-amide in the presence of zinc oxide or zinc hydroxide. The particular details of such methods are known in the art.

The following examples illustrate the principles and advantages of the invention.

EXAMPLES

Several assay methods were used in the following examples to follow the reaction progress and to determine nitrile hydratase and amidase activities during the enzymatic conversion of 2-hydroxy-4-(methylthio)-butanenitrile to the corresponding amide and/or acid. An early HPLC assay was adapted from those reported for use with 2-hydroxy-4-(methylthio)-butanoic acid (HMB-acid) (J. Ag. Food Chem., 35: 692–694, 1987). The corresponding nitrile (HMB-nitrile) and amide (HMB-amide) precursors were readily separated from the acid, allowing for determination of the amount of acid formed therefrom. In a modified HPLC assay, a sample was prepared by mixing solution being analyzed with one fourth volume 5 N HCl, diluting in water to about 1 mM, and microfiltering. The sample was loaded in a HPLC column (Phenomenex Selectosil 5, C18, 100 Å 3.2×250 mm) and eluted using a 15% aqueous acetonitrile solvent at a flow rate of 1.0 ml/min. Detection was at 214 nm absorbance, 0.05 AUFS. Retention times were: HMB-acid—at the solvent front (approx. 1.5 min.); HMB-acid dimer—1.8 min.; HMB-amide—3.0 min.; and HMB-nitrile—7.8 min. In an alternative assay, simultaneous separation and quantification of 2-hydroxy-4-(methylthio)-butanoic acid and the corresponding nitrile and amide was effected by gas chromatographic (GC) methods using trimethylsilyl derivatives thereof.

The examples presented below which report data relater only to strain 52 cells and enzymes derived therefrom is representative of data related to strain 56 wt cells and enzymes, as well.

Example 1

Strains 52 and 56 wt Have Nitrile Hydratase and Amidase Activities

Initial screenings, through which strains 52 and 56 wt were selected as candidate microbes, demonstrated that whole cells of these strains contained enzymes having nitrile hydratase, amidase and/or nitrilase activities. To verify the activities, strains capable of using nitriles as their sole nitrogen source, including strains 52 and 56 wt, were tested for the ability to convert 2-hydroxy-4-(methylthio)-butanenitrile (HMB-nitrile) to HMB-acid. Strain 52 and 56 wt cells were grown in media containing a carbon source, yeast extract and a utilizable nitrile (e.g. acetonitrile, butyronitrile or benzonitrile). The yeast extract was added as a supplementary source of carbon, nitrogen and vitamins allowing more robust growth of the strains and, perhaps, greater activity of the enzymes of interest. The nitrile was added to induce synthesis of nitrilase. The cells were harvested from the growth culture media and washed free of inducing nitrile.

The cells were then resuspended in a phosphate buffer and mixed with the HMB-nitrile substrate, with the final HMB-nitrile concentration being about 100 mM. The mixture was incubated overnight at 300° C. and then assayed for 2-hydroxy-4-(methylthio)-butanoic acid (HMB-acid) by HPLC. Strains 52 and 56 wt were both able to completely convert HMB-nitrile (100 mM) to its corresponding acid.

Further experiments suggested that enzyme-catalyzed conversion of HMB-nitrile to HMB-acid occurs by a two-step (nitrile hydratase/amidase) process rather than by a single-step (nitrilase) reaction. HMB-nitrile and HMB-amide substrates were mixed with washed whole-cells of strain 52 (and, independently, of strain 56 wt) to establish a substrate concentration of 100 mM. For each strain, approximately 13 mg of cells (dry weight) were used in each 1.0 ml reaction. Aliquots of the reaction mixtures were extracted at various times, and the extracts were derivatized and analyzed by GC.

Figure 1B:
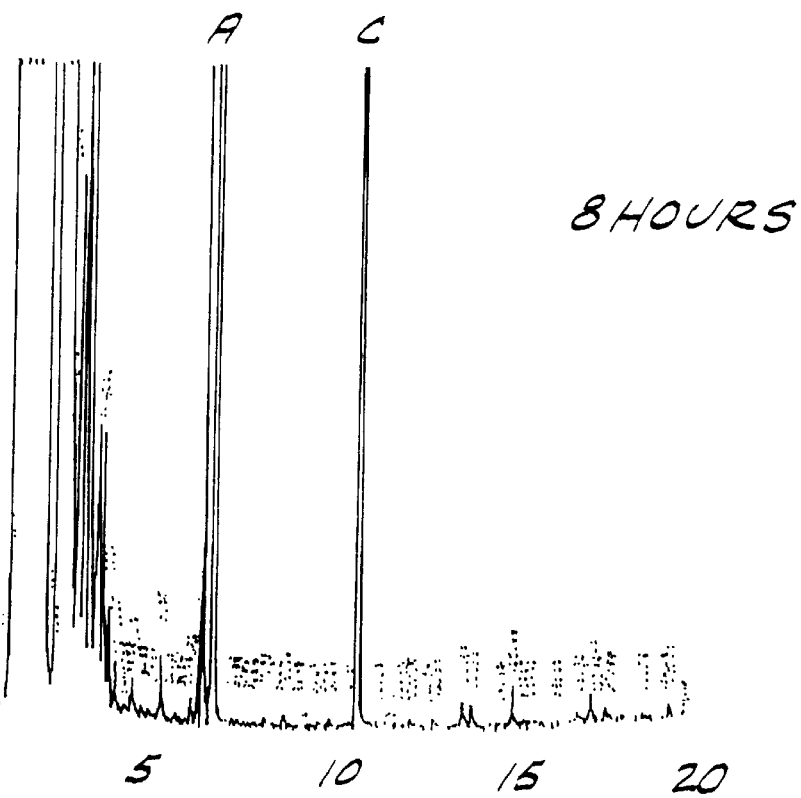

Between about 88% and 98% of HMB-nitrile substrate was converted to a mixture of HMB-amide and HMB-acid within 2 hours, and virtually all (>97%) of the nitrile was converted to HMB-acid within 8 hours. (FIGS. 1A and 1B). When HMB-amide was used as the substrate, about 89%–98% of the amide was converted to HMB-acid within 2 hours, and more than 99% of the amide was converted to the acid within 8 hours. Based on these data, the amide appears to be an intermediate in the conversion of HMB-nitrile to HMB-acid.

Example 2

Isolation and Identification of Microbial Strains 52 and 56 wt

Twenty-one microbial strains, including strains 52 and 56 wt were isolated from natural soil samples based on the ability to use various nitriles as principal nutrient sources of nitrogen and/or carbon. The nitriles included aliphatic nitriles such as acetonitrile and butyronitrile, aromatic nitriles such as benzonitrile and benzyl cyanide, and cyanohydrins such as acetone cyanohydrin, mandelonitrile, lactonitrile and HMB-nitrile. All but one strain used one or more of the nitriles for growth with butyronitrile being the most universally used nitrile. The cyanohydrins were toxic to most of the strains tested.

Strains 52 and 56 wt were characterized and determined to be of genus Rhodococcus. Isolates were subcultured twice, incubated and analyzed using the MIDI/Hewlett Packard Microbial Identification System (MIS) and using the Biolog identification system. The MIS used high resolution gas chromatography to determine the fatty acid profile of the 52 and 56 wt isolate. This fatty acid profile was then compared, using statistical pattern recognition software, to the profiles of known bacteria contained within a database. The results for strain 52, shown in Tables 1a, 1b, 2a, 2b, 3a and 3b, indicate that the bacteria is most closely associated with the genus Rhodococcus. The results for strain 56 wt, shown in Tables 4a and 4b, indicate that this strain is also most closely associated with the genus Rhodococcus. In the Biolog identification system, a microplate comprising 96 microwells was used to test the ability of strains 52 and 56 wt to oxidize 95 different carbon sources. The carbon sources were selected for characterizing and differentiating Gram positive aerobic bacteria. The layout of the microplate is shown in Table 5. The substrate use characteristics of strains 52 and 56 wt were compared to the substrate use of known bacteria in the Biolog database. However, as shown in Tables 6a, 6b, 7a and 7b, the Biolog system was unsuccessful in positively identifying strains 52 and 56 wt, respectively.

TABLE 1a

MIDI/HP Microbial Identification System - Profile Data
Strain 52 - Run #1 (ID: 9614 Bottle: 10 BIOTECH-95292-008)

| RT | Area | Ar/Ht | Respon | ECL | Name | % | Comment 1 | Comment 2 |
|---|---|---|---|---|---|---|---|---|
| 1.597 | 323760896 | 0.032 | . . . | 7.031 | SOLVENT PEAK | . . . | < min rt | |
| 6.898 | 1256 | 0.049 | 0.999 | 14.000 | 14:0 | 0.82 | ECL deviates 0.000 | Reference −0.001 |
| 8.382 | 5040 | 0.045 | 0.962 | 15.000 | 15:0 | 3.17 | ECL deviates 0.000 | Reference −0.001 |
| 9.630 | 2800 | 0.046 | 0.938 | 15.773 | 16:1 w9c | 1.72 | ECL deviates −0.001 | |
| 9.701 | 3704 | 0.042 | 0.937 | 15.817 | Sum In Feature 4 | 2.27 | ECL deviates −0.000 | 16:1 w7c/15 iso 2OH |
| 9.764 | 18312 | 0.047 | 0.936 | 15.856 | Sum In Feature 4 | 11.21 | ECL deviates 0.009 | 15:0 ISO 2OH/16:1w7c |
| 9.996 | 34128 | 0.046 | 0.932 | 15.999 | 16:0 | 20.79 | ECL deviates −0.001 | Reference −0.002 |
| 11.336 | 12336 | 0.061 | 0.913 | 16.792 | 17:1 w8c | 7.36 | ECL deviates 0.000 | |
| 11.689 | 11472 | 0.048 | 0.908 | 17.001 | 17:0 | 6.81 | ECL deviates 0.001 | Reference −0.001 |
| 12.398 | 4816 | 0.048 | 0.900 | 17.411 | 17:0 10 methyl | 2.83 | ECL deviates 0.001 | |
| 13.015 | 43176 | 0.050 | 0.893 | 17.769 | 18:1 w9c | 25.21 | ECL deviates −0.000 | |
| 13.414 | 3008 | 0.054 | 0.889 | 18.000 | 18:0 | 1.75 | ECL deviates −0.000 | Reference −0.002 |
| 14.092 | 26392 | 0.050 | 0.883 | 18.393 | TBSA 10Me18:0 | 15.24 | ECL deviates 0.001 | |
| 14.720 | 1432 | 0.071 | 0.878 | 18.757 | Sum In Feature 8 | 0.82 | ECL deviates 0.001 | unknown 18.756/19:1 |
| ******* | 22016 | . . . | . . . | . . . | SUMMED FEATURE 4 | 13.48 | 16:1 w7c/15 iso 2OH | 15:0 ISO 2OH/16:1w7c |
| ******* | 1432 | . . . | . . . | . . . | SUMMED FEATURE 8 | 0.82 | unknown 18.756/19:1 | 19:1 w11c/unk 18.756 |

TABLE 1b

MIDI/HP Microbial Identification System - Summary
Strain 52 - Run #1 (ID: 9614 Bottle: 10 BIOTECH-95292-008)

| Solvent Ar | Total Area | Named Area | Percent Named | Total Amount | Number Reference | ECL Deviation | Reference ECL Shift |
|---|---|---|---|---|---|---|---|
| 323760896 | 167872 | 167872 | 100.00 | 152969 | 5 | 0.002 | 0.001 |

| | | | |
|---|---|---|---|
| TSBA [Rec 3.90] | Gordona | 0.311 | (Rhodococcus rubropertinctus) |
| | G. rubropertinctus | 0.311 | (Rhodococcus rubropertinctus) |
| | G. bronchialis | 0.248 | (Rhodococcus bronchialis) |
| | Nocardia | 0.290 | |
| | N. asteroides | 0.290 | |
| | N. a. GC subgroup A* | 0.290 | |
| | N. otitidiscaviarum | 0.168 | |
| | N. o. GC subgroup A | 0.168 | |
| CLIN [Rev 3.90] | Rhodococcus | 0.385 | |
| | R. rhodochrous* | 0.385 | |
| UPJ [Rev 1.0] | * NO MATCH * | | |

GRAM RXN G+ RODS

TABLE 2a

MIDI/HP Microbial Identification System - Profile Data
Strain 52 - Run #2 (ID: 9692 Bottle: 12 BIOTECH-CLIN-BTR52-95292-008)

| RT | Area | Ar/Ht | Respon | ECL | Name | % | Comment 1 | Comment 2 |
|---|---|---|---|---|---|---|---|---|
| 1.597 | 334384384 | 0.033 | . . . | 7.030 | . . . . . . . . . | . . . | < min rt | |
| 6.900 | 2688 | 0.041 | 0.993 | 14.000 | 14:0 | 1.60 | ECL deviates 0.000 | Reference 0.001 |
| 9.634 | 1144 | 0.042 | 0.938 | 15.774 | 16:1 w9c | 0.65 | ECL deviates 0.000 | |
| 9.701 | 11504 | 0.047 | 0.937 | 15.816 | Sum In Feature 4 | 6.48 | ECL deviates −0.001 | 16:1 w7c/15 iso 2OH |
| 9.765 | 15008 | 0.047 | 0.936 | 15.855 | Sum In Feature 4 | 8.45 | ECL deviates 0.008 | 15:0 ISO 2OH/16:1w7c |
| 9.998 | 64792 | 0.045 | 0.932 | 16.000 | 16:0 | 36.32 | ECL deviates −0.000 | Reference −0.001 |
| 10.732 | 2456 | 0.048 | 0.923 | 16.434 | 16:0 10 methyl | 1.36 | ECL deviates 0.004 | |
| 11.334 | 1064 | 0.058 | 0.916 | 16.790 | 17:1 w8c | 0.59 | ECL deviates −0.002 | |
| 11.690 | 1288 | 0.051 | 0.912 | 17.001 | 17:0 | 0.71 | ECL deviates 0.001 | Reference 0.000 |
| 12.930 | 680 | 0.042 | 0.900 | 17.718 | Sum In Feature 6 | 0.37 | ECL deviates −0.002 | 18:2 w6, 9c/18:0 ANTE |

TABLE 2a-continued

MIDI/HP Microbial Identification System - Profile Data
Strain 52 - Run #2 (ID: 9692 Bottle: 12 BIOTECH-CLIN-BTR52-95292-008)

| RT | Area | Ar/Ht | Respon | ECL | Name | % | Comment 1 | Comment 2 |
|---|---|---|---|---|---|---|---|---|
| 13.017 | 49688 | 0.050 | 0.899 | 17.769 | 18:1 w9c | 26.87 | ECL deviates −0.000 | |
| 13.416 | 6976 | 0.050 | 0.896 | 18.000 | 18:0 | 3.76 | ECL deviates −0.000 | Reference −0.001 |
| 14.094 | 23984 | 0.050 | 0.891 | 18.393 | TBSA 10Me18:0 | 12.85 | ECL deviates 0.001 | |
| 18.558 | 864 | 0.053 | ... | 20.997 | ......... | ... | > max rt | |
| ******* | 26512 | ... | ... | ... | SUMMED FEATURE 4 | 14.93 | 16:1 w7c/15 iso 2OH | 15:0 ISO 2OH/16:1w7c |
| ******* | 680 | ... | ... | ... | SUMMED FEATURE 6 | 0.37 | 18:2 w6, 9c/18:0 ANTE | 18:0 ANTE/18:2 w6, 9c |

TABLE 2b

MIDI/HP Microbial Identification System - Summary
Strain 52 - Run #2 (ID: 9692 Bottle: 12 BIOTECH-CLIN-BTR52-95292-008)

| Solvent Ar | Total Area | Named Area | Percent Named | Total Amount | Number Reference | ECL Deviation | Reference ECL Shift |
|---|---|---|---|---|---|---|---|
| 334384384 | 181272 | 181272 | 100.00 | 166318 | 4 | 0.003 | 0.001 |

| | | | |
|---|---|---|---|
| TSBA [Rev 3.90] | Nocardia | 0.808 | |
| | N. asteroides | 0.808 | |
| | N. a. GC subgroup A* | 0.808 | |
| | N. carnea | 0.638 | (72h-96h) |
| CLIN [Rev 3.90] | Rhodococcus | 0.822 | |
| | R. rhodochrous* | 0.822 | |
| | R. rhodnii | 0.431 | |
| | Nocardia | 0.574 | |
| | N. asteroides | 0.574 | |
| | N. a. GC subgroup A* | 0.574 | |

TABLE 3a

MIDI/HP Microbial Identification System - Profile Data
Strain 52 - Run #3 (ID: 10867 Bottle: 6 BIOTECH-52--96145-004)

| RT | Area | Ar/Ht | Respon | ECL | Name | % | Comment 1 | Comment 2 |
|---|---|---|---|---|---|---|---|---|
| 1.634 | 379091200 | 0.033 | ... | 7.027 | SOLVENT PEAK | ... | < min rt | |
| 2.232 | 528 | 0.026 | ... | 8.311 | ......... | ... | < min rt | |
| 6.905 | 2560 | 0.044 | 0.996 | 14.000 | 14:0 | 1.02 | ECL deviates −0.000 | Reference −0.004 |
| 8.384 | 6896 | 0.044 | 0.964 | 15.000 | 15:0 | 2.67 | ECL deviates 0.000 | Reference −0.004 |
| 9.628 | 3712 | 0.047 | 0.944 | 15.773 | 16:1 w9c | 1.41 | ECL deviates −0.001 | |
| 9.697 | 9944 | 0.045 | 0.943 | 15.816 | Sum In Feature 4 | 3.76 | ECL deviates −0.001 | 16:1 w7c/15 iso 2OH |
| 9.761 | 24688 | 0.050 | 0.942 | 15.856 | Sum In Feature 4 | 9.33 | ECL deviates 0.009 | 15:0 ISO 2OH/16:1w7c |
| 9.993 | 61624 | 0.048 | 0.938 | 16.000 | 16:0 | 23.20 | ECL deviates −0.000 | Reference −0.005 |
| 10.723 | 2208 | 0.087 | 0.929 | 16.433 | 16:0 10 methyl | 0.82 | ECL deviates 0.003 | |
| 11.328 | 19432 | 0.059 | 0.922 | 16.791 | 17:1 w8c | 7.19 | ECL deviates −0.001 | |
| 11.680 | 17424 | 0.049 | 0.918 | 17.000 | 17:0 | 6.42 | ECL deviates −0.000 | Reference −0.006 |
| 12.389 | 5672 | 0.051 | 0.911 | 17.411 | 17:0 10 methyl | 2.07 | ECL deviates 0.001 | |
| 13.007 | 75768 | 0.053 | 0.906 | 17.769 | 18:1 w9c | 27.54 | ECL deviates 0.000 | |
| 13.405 | 8728 | 0.051 | 0.903 | 18.000 | 18:0 | 3.16 | ECL deviates 0.000 | Reference −0.006 |
| 14.083 | 29600 | 0.052 | 0.898 | 18.394 | TBSA 10Me18:0 | 10.66 | ECL deviates 0.002 | |
| 14.709 | 2088 | 0.071 | 0.894 | 18.757 | Sum In Feature 8 | 0.75 | ECL deviates 0.001 | unknown 18.756/19:1 |
| 18.350 | 6568 | 0.182 | ... | 20.887 | ......... | ... | > max rt | |
| 19.122 | 3336 | 0.151 | ... | 21.339 | ......... | ... | > max rt | |
| ******* | 34632 | ... | ... | ... | SUMMED FEATURE 4 | 13.09 | 16:1 w7c/15 iso 2OH | 15:0 ISO 2OH/16:1w7c |
| ******* | 2088 | ... | ... | ... | SUMMED FEATURE 8 | 0.75 | unknown 18.756/19:1 | 19:1 w11c/unk 18.756 |

TABLE 3b

MIDI/HP Microbial Identification System - Summary
Strain 52 - Run #3 (ID: 10867 Bottle: 6 BIOTECH-52--96145-004)

| Solvent Ar | Total Area | Named Area | Percent Named | Total Amount | Number Reference | ECL Deviation | Reference ECL Shift |
|---|---|---|---|---|---|---|---|
| 379091200 | 270344 | 270344 | 100.00 | 249235 | 5 | 0.003 | 0.005 |

| TSBA [Rev 3.90] | | | |
|---|---|---|---|
| | Gordona | 0.500 | (*Rhodococcus bronchialis*) |
| | *G. bronchialis* | 0.500 | (*Rhodococcus bronchialis*) |
| | *G. rubropertinctus* | 0.413 | (*Rhodococcus rubropertinctus*) |
| | Nocardia | 0.458 | |
| | *N. asteroides* | 0.458 | |
| | *N. a.* GC subgroup A* | 0.458 | |
| | *N. otitidiscaviarum* | 0.305 | |
| | *N. o.* GC subgroup A | 0.305 | |

GRAM RXN G+ RODS

TABLE 4a

MIDI/HP Microbial Identification System - Profile Data
Strain 56wt - Run #1 (ID: 10866 Bottle: 5 BIOTECH 56WT-96145-005)

| RT | Area | Ar/Ht | Respon | ECL | Name | % | Comment 1 | Comment 2 |
|---|---|---|---|---|---|---|---|---|
| 1.633 | 369924352 | 0.033 | ... | 7.025 | SOLVENT PEAK | ... | < min rt | |
| 2.231 | 656 | 0.027 | ... | 8.309 | ......... | ... | < min rt | |
| 6.905 | 3384 | 0.045 | 0.996 | 14.000 | 14:0 | 1.48 | ECL deviates 0.000 | Reference −0.004 |
| 8.239 | 1176 | 0.046 | 0.967 | 14.903 | 15:1 w5c | 0.50 | ECL deviates −0.001 | |
| 8.382 | 10872 | 0.046 | 0.964 | 14.999 | 15:0 | 4.59 | ECL deviates −0.001 | Reference −0.005 |
| 9.627 | 2008 | 0.044 | 0.944 | 15.773 | 16:1 w9c | 0.83 | ECL deviates −0.001 | |
| 9.697 | 9344 | 0.045 | 0.943 | 15.817 | Sum In Feature 4 | 3.86 | ECL deviates −0.000 | 16:1 w7c/15 iso 2OH |
| 9.760 | 26720 | 0.049 | 0.942 | 15.856 | Sum In Feature 4 | 11.03 | ECL deviates 0.009 | 15:0 ISO 2OH/16:1w7c |
| 9.993 | 51768 | 0.048 | 0.938 | 16.000 | 16:0 | 21.30 | ECL deviates 0.000 | Reference −0.005 |
| 10.722 | 4168 | 0.064 | 0.929 | 16.433 | 16:0 10 methyl | 1.70 | ECL deviates 0.003 | |
| 11.329 | 22320 | 0.057 | 0.922 | 16.792 | 17:1 w8c | 9.02 | ECL deviates 0.000 | |
| 11.680 | 15664 | 0.051 | 0.918 | 17.000 | 17:0 | 6.31 | ECL deviates 0.000 | Reference −0.006 |
| 12.387 | 13992 | 0.051 | 0.911 | 17.410 | 17:0 10 methyl | 5.59 | ECL deviates 0.000 | |
| 13.005 | 41880 | 0.053 | 0.906 | 17.768 | 18:1 w9c | 16.63 | ECL deviates −0.001 | |
| 13.404 | 4216 | 0.054 | 0.903 | 18.000 | 18:0 | 1.67 | ECL deviates −0.000 | Reference −0.007 |
| 14.082 | 37056 | 0.052 | 0.898 | 18.393 | TBSA 10Me18:0 | 14.59 | ECL deviates 0.001 | |
| 14.707 | 1216 | 0.063 | 0.894 | 18.756 | Sum In Feature 8 | 0.48 | ECL deviates 0.000 | unknown 18.756/19:1 |
| 15.127 | 1088 | 0.055 | 0.891 | 19.000 | 19:0 | 0.43 | ECL deviates 0.000 | Reference −0.008 |
| 18.545 | 1456 | 0.080 | ... | 21.001 | ......... | ... | > max rt | |
| ******* | 36064 | ... | ... | ... | SUMMED FEATURE 4 | 14.90 | 16:1 w/7c/15 iso 2OH | 15:0 ISO 2OH/16:1w7c |
| ******* | 1216 | ... | ... | ... | SUMMED FEATURE 8 | 0.48 | unknown 18.756/19:1 | 19:1 w11c/unk 18.756 |

TABLE 4b

MIDI/HP Microbial Identification System - Summary
Strain 56wt - Run #1 (ID: 10866 Bottle: 5 BIOTECH 56WT-96145-005)

| Solvent Ar | Total Area | Named Area | Percent Named | Total Amount | Number Reference | ECL Deviation | Reference ECL Shift |
|---|---|---|---|---|---|---|---|
| 369924352 | 246872 | 246872 | 100.00 | 228080 | 6 | 0.002 | 0.006 |

| TSBA [Rev 3.90] | | | |
|---|---|---|---|
| | Rhodococcus | 0.212 | |
| | *R. rhodnii* | 0.212 | |
| | *R. erythropolis* | 0.117 | (some 48h) |
| | Gordona | 0.187 | (*Rhodococcus bronchialis*) |
| | *G. bronchialis* | 0.187 | (*Rhodococcus bronchialis*) |

GRAM RXN G+ RODS

TABLE 5

Biolog Identification System - GP Microplate

| A1 | A2 | A3 | A4 | A5 | A6 |
|---|---|---|---|---|---|
| water | α-cyclodextrin | β-cyclodextrin | dextrin | glycogen | inulin |
| B1 | B2 | B3 | B4 | B5 | B6 |

TABLE 5-continued

Biolog Identification System - GP Microplate

| | | | | | |
|---|---|---|---|---|---|
| L-arabinose | D-arabitol | arbutin | cellobiose | D-fructose | L-fucose |
| C1 | C2 | C3 | C4 | C5 | C6 |
| α-D-lactose | lactulose | maltose | maltotriose | D-mannitol | D-mannose |
| D1 | D2 | D3 | D4 | D5 | D6 |
| β-methyl D-glucoside | α-methyl D-mannoside | palatinose | D-psicose | D-raffinose | L-rhamnose |
| E1 | E2 | E3 | E4 | E5 | E6 |
| D-tagatose | D-trehalose | turanose | xylitol | D-xylose | acetic acid |
| F1 | F2 | F3 | F4 | F5 | F6 |
| lactamide | D-lactic acid methyl ester | L-lactic acid | D-malic acid | L-malic acid | methyl pyruvate |
| G1 | G2 | G3 | G4 | G5 | G6 |
| alaninamide | D-alanine | L-alanine | L-alanyl-glycine | L-asparagine | L-glutamic acid |
| H1 | H2 | H3 | H4 | H5 | H6 |
| adenosine | 2'-deoxy | inosine | thymidine | uridine | adenosine-5'-monophosphate |
| A7 | A8 | A9 | A10 | A11 | A12 |
| mannan | tween 40 | tween 80 | n-acetyl glucosamine | N-acetyl mannosamine | amygdalin |
| B7 | B8 | B9 | B10 | B11 | B12 |
| D-galactose | D-galacturonic acid | gentiobiose | D-gluconic acid | α-D-glucose | m-inositol |
| C7 | C8 | C9 | C10 | C11 | C12 |
| D-melezitose | D-melibiose | α-methyl D-galactoside | β-methyl D-galactoside | 3-methyl glucose | α-methyl D-glucoside |
| D7 | D8 | D9 | D10 | D11 | D12 |
| D-ribose | salicin | sedoheptulosan | D-sorbitol | stachyose | sucrose |
| E7 | E8 | E9 | E10 | E11 | E12 |
| α-hydroxy-butyric acid | β-hydroxy-butyric acid | γ-hydroxy-butyric acid | p-hydroxy-phenyl acetic acid | α-keto glutaric acid | α-keto valeric acid |
| F7 | F8 | F9 | F10 | F11 | F12 |
| methyl succinate | propionic acid | pyruvic acid | succinamic acid | succinic acid | N-acetyl L-glutamic acid |
| G7 | G8 | G9 | G10 | G11 | G12 |
| glycyl-L-glutamic acid | L-pyroglutamic acid | L-serine | putrescine | 2,3-butanediol | glycerol |
| H7 | H8 | H9 | H10 | H11 | H12 |
| thymidine-5'-monophosphate | uridine-5'-monophosphate | fructose-6-phosphate | glucose-1-phosphate | glucose-6-phosphate | D-L-α-glycerol phospahte |

TABLE 6a

Biolog Identification System - Utilization Data
Strain 52 (BIOTECH-BTR-52-95292-008)

MICROLOG (TM) 3 RELEASE 3.50
POSITIVE/NEGATIVE DATA
 XXX  = percent change in optical density versus A1 control well
<XXX> = positive, {XXX} = borderline, XXX = negative
−XXX  = percent change negative
XXX+ = data negative or borderline, "=>" ID choice positive >90% of time
XXX− = data positive or borderline, "=>" ID choice positive <10% of time

| | 1 | 2 | 3 | 4 | 5 | 6 | 7 | 8 | 9 | 10 | 11 | 12 |
|---|---|---|---|---|---|---|---|---|---|---|---|---|
| A | 0 | 0 | 0 | 0 | 0 | 0 | 0 | <100> | <100> | 0+ | 0 | 0 |
| B | 0 | <100> | 0 | 0 | <100> | 0 | 0 | 0 | 0 | 0+ | 0+ | 0 |
| C | 0 | 0 | 0 | 0 | <100> | <100> | <100> | 0 | 0 | 0 | 0 | 0 |
| D | 0 | 0 | 0 | <100> | <100> | <100> | <100> | <100> | <100> | <100> | 0 | 0 |
| E | 0 | <100> | <100> | <100> | <100> | <100> | <100> | <100> | 0 | 0 | 0 | <100> |
| F | 0 | <100> | <100> | <100> | <100> | <100> | <100> | <100> | <100> | <100> | <100> | <100> |
| G | <100> | 0 | 0 | 0 | 0+ | 0 | <100> | <100> | <100> | 0+ | 0 | 0 |
| H | 0 | 0 | 0 | <100− | <100− | 0 | 0 | 0 | 0 | 0 | 0 | 0 |

BIO-NUMBER: 0030-2200-0340-0774-3761-3777-4070-0600

TABLE 6b

Biolog Identification System - Summary
Strain 52 (BIOTECH-BTR-52-95292-008)
NO IDENTIFICATION
"SIM" <0.50

| CLOSEST-SPECIES: | SIM | DIST | AVG | MAX |
|---|---|---|---|---|
| => 1) RHODOCOCCUS ERYTHROPOLIS | 0.192 | 12.314 | 0.070 | 0.694 |
| 2) RHODOCOCCUS FASCIANS | 0.086 | 12.576 | 0.188 | 2.706 |
| 3) CORYNEBACTERIUM VARIABILIS | 0.014 | 13.166 | 0.250 | 1.587 |
| 4) GORDONA SPUTI | 0.002 | 13.863 | 0.219 | 1.469 |
| 5) CORYNEBACTERIUM NITRILOPHILUS | 0.000 | 14.305 | 0.500 | 1.725 |
| 6) GORDONA TERRAE | 0.000 | 14.491 | 0.063 | 0.119 |
| 7) RHODOCOCCUS OBUENSIS | 0.000 | 14.716 | 3.245 | 12.156 |
| 8) CDC GROUP F-1 SUBGROUP B | 0.000 | 15.185 | 0.344 | 1.106 |
| 9) RHODOCOCCUS MARIS | 0.000 | 15.895 | 0.094 | 0.606 |
| 10) CORYNEBACTERIUM UREALYTICUM | 0.000 | 16.401 | 0.750 | 1.212 |
| Other: | — | — | — | — |

TABLE 7a

Biolog Identification System - Utilization Data
Strain 56wt (BIOTECH-WT-56-96145-005)

MICROLOG (TM) 3 RELEASE 3.50
POSITIVE/NEGATIVE DATA
  XXX  = percent change in optical density versus A1 control well
  <XXX> = positive, {XXX} = borderline, XXX = negative
  -XXX  = percent change negative
  XXX+ = data negative or borderline, "=>" ID choice positive >90% of time
  XXX- = data positive or borderline, "=>" ID choice positive <10% of time

|   | 1 | 2 | 3 | 4 | 5 | 6 | 7 | 8 | 9 | 10 | 11 | 12 |
|---|---|---|---|---|---|---|---|---|---|---|---|---|
| A | 0 | <100> | <100- | { 50+ | 0 | 0 | 0 | <100> | <100> | 0 | <100- | <100- |
| B | <100- | <100- | <100- | 0 | <100> | 0 | 0 | 0 | 0 | 0 | 0+ | <100- |
| C | <100> | 0 | 0 | 0 | <100- | <100> | 0 | 0 | 0 | 0 | { 50- | <100- |
| D | <100- | 0 | 0 | <100> | 0 | 0 | { 50} | <100> | 0 | <100> | { 50- | <100- |
| E | <100- | 0 | 0 | <100> | 0 | <100> | <100> | <100> | <100> | 0 | <100- | <100- |
| F | <100> | <100> | <100> | 0 | <100> | <100> | <100> | <100> | <100> | <100- | <100> | <100> |
| G | <100> | 0 | 0 | 0 | 0 | 0 | 0 | <100> | 0 | 0 | <100- | <100> |
| H | <100> | <100> | <100> | <100> | <100> | <100- | <100- | <100> | <100> | <100> | <100> | <100> |

BIO-NUMBER: 3433-7201-4303-4467-4573-7377-4023-7777

TABLE 7b

Biolog Identification System - Summary
Strain 56wt (BIOTECH-WT-56-96145-005)
NO IDENTIFICATION
"SIM" <0.50

| CLOSEST-SPECIES: | SIM | DIST | AVG | MAX |
|---|---|---|---|---|
| => 1) MICROCOCCUS VARIANS | 0.007 | 19.957 | 0.078 | 0.344 |
| 2) RHODOCOCCUS FASCIANS | 0.003 | 24.399 | 0.109 | 0.331 |
| 3) STAPHYLOCCCCUS SCHLEIFERI SS COAGULANS | 0.002 | 25.268 | 0.208 | 1.125 |
| 4) STAPHYLOCOCCUS AUREUS | 0.002 | 26.433 | 0.438 | 11.669 |
| 5) STAPHYLOCOCCUS KLOOSII B | 0.002 | 26.615 | 0.406 | 3.419 |
| 6) STAPHYLOCOCCUS SCIURI | 0.001 | 27.142 | 0.792 | 2.088 |
| 7) STAPHYLOCOCCUS DELPHINI | 0.001 | 27.766 | 0.333 | 6.287 |
| 8) STAPHYLOCOCCUS FELIS | 0.001 | 28.490 | 0.275 | 0.663 |
| 9) CORYNEBACTERIUM NITRILOPHILUS | 0.001 | 28.492 | 2.785 | 11.024 |
| 10) STAPHYLOCOCCUS EPIDERMIDIS B | 0.001 | 28.557 | 0.703 | 1.931 |
| Other: | — | — | — | — |

Example 3

Effect of Inducer Concentration and Cobalt in Growth Medium on Nitrile Hydratase Activities The effect of culturing strain 52 and 56 wt cells in the presence of an inducer, butyronitrile, and an activity enhancer, cobalt, on nitrile hydratase activity was investigated. As indicated in Table 8, the nitrile hydratase activity was slightly higher at lower concentrations of butyronitrile, while the addition of cobalt had a slight positive effect on activity.

TABLE 8

Effect of Butyronitrile Inducer and Cobalt
on Strain 52 Nitrile Hydratase Activity

| Growth Condition | Nitrile Hydratase Specific Activity ($\mu$mole min$^{-1}$/g) |
|---|---|
| 0.2% butyronitrile | 216 |
| 0.4% butyronitrile | 154 |
| 0.2% butyronitrile + 10 mM cobalt | 247 |

Example 4

Stability of Catalyst at Various Conditions

A set of experiments were performed to study the innate stability of the whole-cell biocatalyst. In the first experiment, cells were incubated in buffer for 0, 1, 2 or 18 hours at either 2.5° C. or 22° C. In the second experiment, cell suspensions were stored up to one week at either 4° C. or −20° C. (frozen). Very little difference in activity was observed after storage under any of the various conditions.

Example 5

Figure 2:
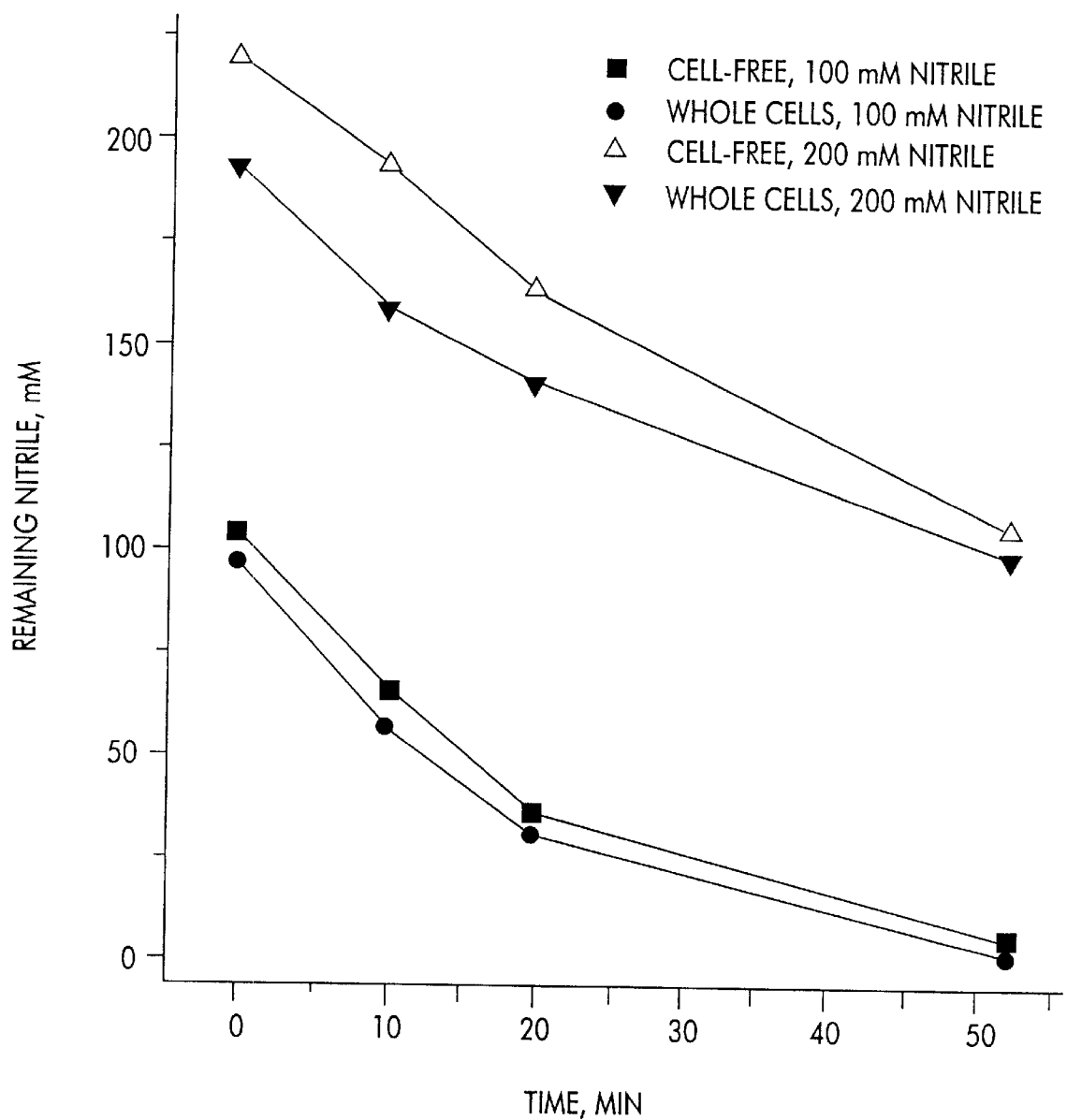
FIG. 2 is a graph showing the reaction progress for the bioconversion of untreated 2-hydroxy-4-(methylthio)-butanenitrile (HMB-nitrile) (100 mM, 200 mM) to HMB-amide in the presence of strain 52 whole cells or cell-free extracts.

Nitrile Hydratase Activity in Whole Cell Suspensions, Cell Lysates and Immobilized Cells The activity of the enzyme derived from cell-free extracts of strain 52 cells was indistinguishable with the activity of enzymes derived from whole cells. Cell-free extracts were prepared by passing cultured cells through a French press and centrifuging the lysed cells to remove cell debris. The nitrile hydratase was assayed using the cleared lysate or an equivalent amount of whole cells in reactions containing either 100 or 200 mM HMB nitrile. As indicated in FIG. 2, the kinetics of nitrile degradation were similar whether catalyzed by the cell-free extract or by whole cells. These results demonstrate that transport of substrate into the cells or of product out of the cells is not a rate-limiting factor in the reaction and that any inhibition observed is directed at the enzyme. In addition, these data indicate that the enzyme is soluble and cytosolic and that either whole cells or lysates thereof may also be used in the conversion reaction without a loss of activity.

Further experiments demonstrated that immobilized cells also maintain nitrile hydratase activity. Strain 52 and 56 wt cells were immobilized in calcium alginate. Cells of strain 52 and 56 wt were grown in 30 ml phosphate/yeast extract/0.5% succinate/0.2% butyronitrile medium at 28° C. The cells were harvested and resuspended in 5 ml of 2% (w/v) sodium alginate in 150 mM NaCl, 10 mM N-(2-hydroxyethyl)piperazine-N'-(2-ethanesulfonic acid) (HEPES), pH 7.0. The resulting cell suspensions were each dropped through a 22 gauge needle into 15 ml of ice-cold CaCl$_2$ (0.2M) with constant slow stirring. Excess CaCl$_2$ was decanted, and the resulting beads were washed with distilled water. The beads were suspended in distilled water and stored at 4° C. until use. Beads of the immobilized cells were counted and placed in one ml of an aqueous 100 mM HMB-nitrile solution. After a two-hour incubation, approximately 20–35% of the nitrile was consumed when ten beads were used, and 40–70% was consumed when twenty beads were used.

Example 6

Effect of 2-Hydroxy-4-(methylthio)-butanenitrile on Nitrile Hydratase and Amidase Activities 2-Hydroxy-4-(methylthio)-butanenitrile (HMB-nitrile) was combined with about 8 mg, dry weight, of washed cells of strains 52/56 wt in sufficient 0.1M Na$_2$HPO$_4$/KH$_2$PO$_4$ buffer (pH 7.1) to form a 1 ml reaction mixture. The reaction was allowed to proceed overnight at 28° C. Samples were withdrawn at various times and extracted with ethyl acetate. The ethyl acetate extracts were derivatized with a silylating reagent (BSTFA/10% TMCS, Pierce Chemical Co. Catalog No. 38841) and analyzed by gas chromatography to quantitate HMB-nitrile, HMB-amide and HMB-acid. The enzymes from strains 52 and 56 wt behaved similarly.

The results, shown for strain 52 in Table 9, demonstrate that in the presence of about 100 mM HMB-nitrile substrate, both the nitrile hydratase and the amidase were active and resulted in virtually all of the substrate being converted to HMB-acid. The nitrile hydratase remained reasonably active at about 200 mM HMB-nitrile, but became nearly inactive at about 500 mM HMB-nitrile. The amidase, while active at about 100 mM HMB-nitrile, was significantly inhibited at HMB-nitrile concentrations of about 200 mM.

TABLE 9

Effect af HMB-Nitrile Concentratian on Strain 52
Nitrilase Hydratase and Amidase Activities

| Initial HMB-Nitrile Concentration, mM | Product Observed, mM | | |
|---|---|---|---|
| | HMB-Nitrile | HMB-Amide | HMB-Acid |
| 100 | 0 | 0 | 120 |
| 200 | 91.5 | 71.4 | 0 |
| 500 | 596 | 9.7 | 0 |
| 1000 | 1223 | 4.3 | 0 |

The inhibiting effect of HMB-nitrile on nitrile hydratase activity was also demonstrated in another set of experiments, in which the initial reaction rate for conversion of HMB-nitrile to HMB-amide in the presence of strain 52 cells was determined at various initial concentrations of HMB-nitrile substrate. The results are shown in Table 10 and presented graphically in FIG. 3.

TABLE 10

Effect of HMB-Nitrile Concentration
on Strain 52 Nitrile Hydratase Activity

| Nitrile Concentration, mM | Initial Rate, $\mu$mol min$^{-1}$ ml$^{-1}$ | Time Interval for Measurement, sec. | Specific Activity, U/g$^a$ |
|---|---|---|---|
| 10 | 14.4 | 0–30 | 2030 |
| 20 | 14.4 | 0–30 | 2030 |
| 40 | 14.0 | 0–30 | 1970 |
| 60 | 12.4 | 0–30 | 1750 |
| 80 | 6.0 | 0–120 | 850 |
| 100 | 5.0 | 0–120 | 700 |
| 125 | 4.5 | 0–120 | 630 |
| 150 | 2.5 | 0–120 | 350 |
| 200 | 2.0 | 0–120 | 280 |

$^a$U = ($\mu$mole min$^{-1}$)

In a further set of experiments, the amidase activity of enzymes from strains 52 and 56 wt were reduced by about 85% to 90% by the presence of HMB-nitrile substrate (100 mM) relative to a reaction in which HMB-amide is converted to the corresponding acid in the absence of HMB-nitrile.

Example 7

Substrate Inhibition of Nitrile Hydratase Activity

Experiments confirmed that the observed inhibition of nitrile hydratase activity was due to the HMB-nitrile substrate rather than the innate instability of the microbial enzyme. Substrate inhibition was at least partially caused by the presence of its corresponding aldehyde and HCN, with hydrogen cyanide being the more significant contributor to the inhibition.

In a first set of experiments, strain 52 whole cells were incubated in a solution consisting of 100 mM 2-hydroxy-4-(methylthio)-butanenitrile (HMB-nitrile) in 0.1M $Na_2HPO_4$/$KH_2PO_4$ buffer, pH 7.1, for various lengths of time. After incubation, the cells were recovered by centrifugation and used to catalyze the hydration of HMB-nitrile. As a control, strain 52 whole cells were incubated in buffer, but without HMB-nitrile, prior to use in an equivalent hydrolysis reaction. The nitrile hydration rate was determined. The results, shown in FIG. 4, indicate that whereas incubation of the cells in buffer for up to two hours had very little effect on reaction rate, incubation of the cells in 100 mM HMB-nitrile resulted in a pronounced decrease in the reaction rate. Moreover, the decrease in reaction rate appeared to be independent of the time of incubation. Under the conditions of these assays, preincubation in 100 mM HMB-nitrile resulted in approximately 50% diminution of catalytic activity: the average initial reaction rates for the HMB-nitrile incubated reactions were 4.0 mmol $min^{-1}$ $mL^{-1}$, whereas the rates for the control reactions were 8.1 mmol $min^{-1}$ $mL^{-1}$. Another set of experiments demonstrated the innate stability of the whole cell biocatalyst under various storage conditions. (Example 3).

Figure 5A:
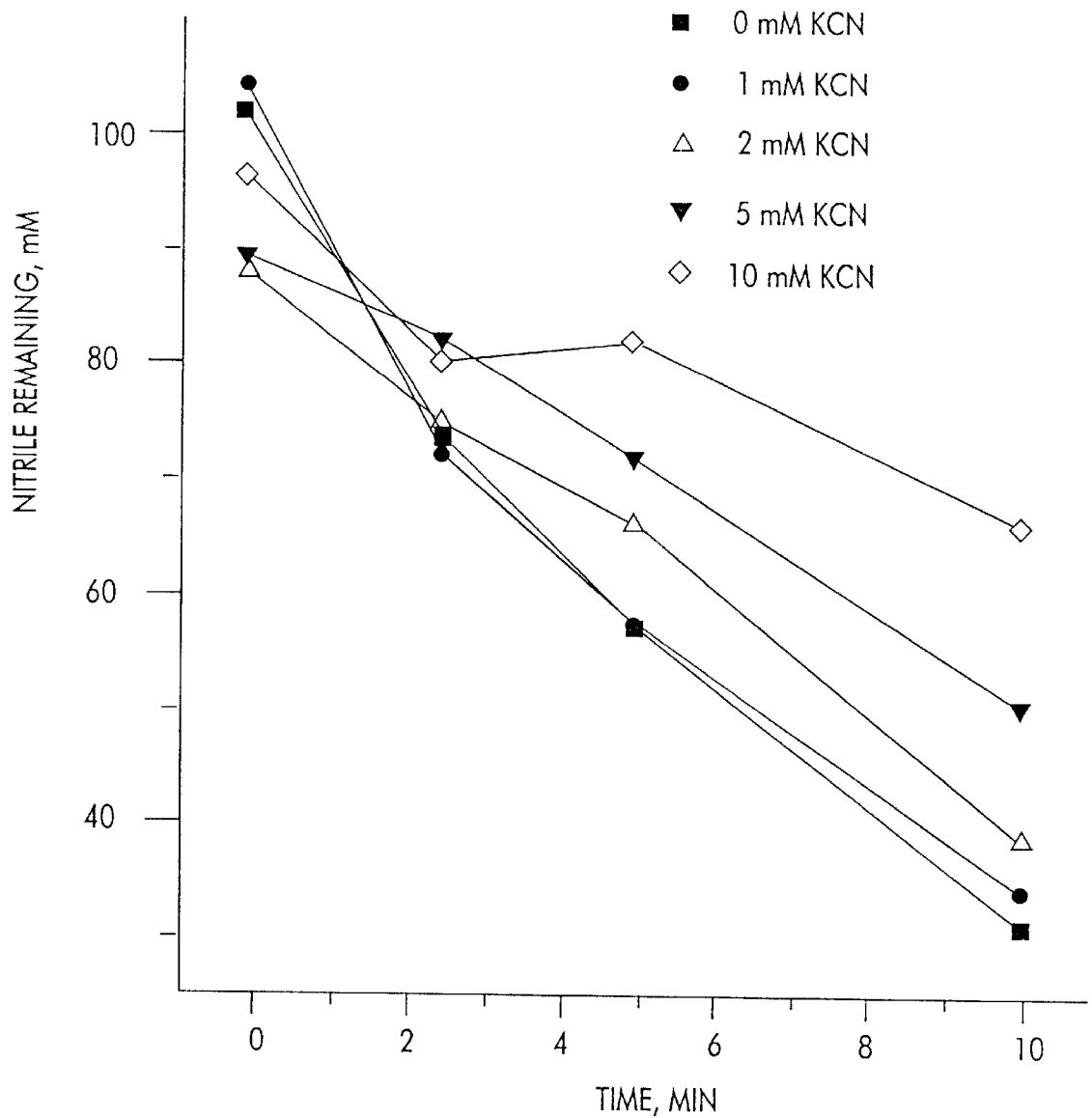
Figure 6:
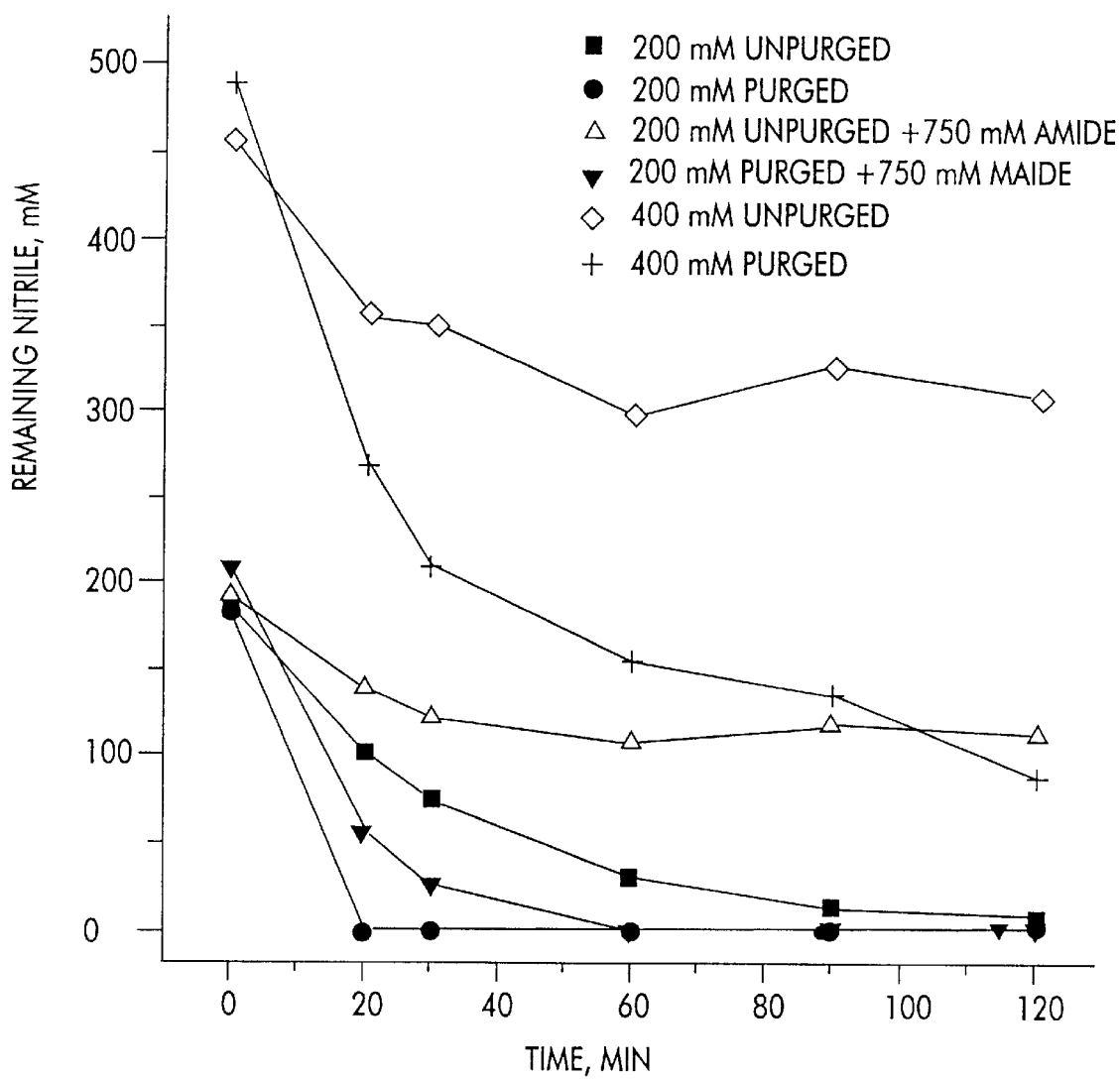
FIG. 6 is a graph showing the reaction progress for the bioconversion of 2-hydroxy-4-(methylthio)-butanenitrile (HMB-nitrile) to HMB-amide using strain 52 whole cells. In separate experimental runs, the HMB-nitrile was supplied to the reaction zone either directly as untreated HMB-nitrile or after a nitrogen-sparging pretreatment to form a reaction solution of various nitrile concentrations (200 mM, 400 mM). In two runs, HMB-amide (750 mM) was also supplied to the reaction zone.

The effect of the decomposition products of HMB-nitrile, HCN and 3-methylthiopropionaldehyde (MMP), on catalytic activity were investigated. To examine hydrogen cyanide inhibition of the nitrile hydratase activity of strain 52 whole cells, HMB-nitrile was hydrated: (1) using whole-cell catalyst in the presence of cyanide at various concentrations; and (2) using whole-cell catalyst which had been preincubated with cyanide at various concentrations for one hour prior to carrying out the reaction. The results from these experiments, shown in FIGS. 5A and 5B, respectively, indicate that cyanide has a negative effect on nitrile hydratase activity, regardless of whether the cyanide was present during the reaction or was present in the cell suspension prior to the reaction. For both cases, the reaction rate in the presence of 10 mM KCN was about half that observed in the absence of KCN. In another set of experiments, about 98% of the cyanide was removed from HMB-nitrile by purging with nitrogen prior to hydration of HMB-nitrile. Because regeneration of cyanide by subsequent decomposition of the HMB-nitrile was relatively slow, subsequent hydration reactions were carried out at 28° C. using either untreated HMB-nitrile or nitrogen-purged HMB-nitrile having reduced amounts of cyanide relative to untreated nitrile. For two reactions, HMB-amide (750 mM) was added to the reaction solution. As shown in FIG. 6, the nitrile hydratase activity of the strain 52 biocatalyst on nitrogen-purged HMB-nitrile was about two-fold higher than the activity observed using unpurged HMB-nitrile, even for the reactions performed in the presence of HMB-amide at a concentration of about 75% of its saturation concentration. Consistently, when hydrogen cyanide is removed, relatively higher concentrations of HMB-nitrile can be converted to HMB-amide without the previously observed inhibitory effect.

The effect of 3-methylthiopropionaldehyde (MMP) was tested by hydrating HMB-nitrile using strain 52 whole-cell catalyst in the presence of various concentrations of MMP (10–40 mM). No differences were observed in rate or extent of the hydration reaction compared with control experiments in which no aldehyde was added to the reaction mixture. In further experiments, in which MMP and cyanide were both added to reaction mixtures, the inhibitory effect of cyanide was observed, but no cumulative effect was observed.

Example 8

Effect of 2-Hydroxy-4-(methylthio)-butaneamide on Nitrile Hydratase and Amidase Activities Experimental data indicated that nitrile hydratase activity is relatively uninhibited by the presence of the amide product being formed—even at saturation conditions of amide. 2-Hydroxy-4-(methylthio)-butanenitrile (HMB-nitrile) was hydrated in an aqueous reaction solution in the presence of strain 52 or strain 56 wt whole cells and in the presence of various concentrations of HMB-amide. In a first set of experiments, 100 mM HMB-nitrile was hydrated using strains 52 or 56 wt at a temperature of 28° C. with initial HMB-amide concentrations in the reaction mixture of 0 mM, 200 mM, 500 mM, 1000 mM and 1500 mM. The results, shown in Table 11, indicated that both strains 52 and 56 wt converted 100 mM HMB-nitrile to HMB-amide even in the presence of 1.5M HMB-amide. These experiments were repeated using 200 mM HMB-nitrile with strain 52 cells. As shown in Table 12, the enzymes derived from strain 52 cells exhibited nitrile hydratase activity for converting 200 mM HMB-nitrile in the presence of 1.5M HMB-amide. However, a comparison of Table 11 and Table 12 suggests that the extent of conversion at higher HMB-amide concentrations may be less for the conversion of 200 mM HMB-nitrile as compared to the conversion of 100 mM HMB-nitrile.

TABLE 11

Conversion of 100 mM HMB-Nitrile to HMB-Amide in the Presence of Various Amide Concentrations

| | | Product Observed (mM) after 3.5 hr | | |
|---|---|---|---|---|
| Strain | Initial Amide (mM) | Nitrile | Amide | Acid |
| 52 | 0 | 0 | 0 | 96 |
| | 200 | 0 | 113 | 168 |
| | 500 | 0 | 539 | 0 |
| | 1000 | 2 | 877 | 0 |
| | 1500 | 8 | 1109 | 0 |
| 56wt | 0 | 0 | 0 | 97 |
| | 290 | 0 | 91 | 204 |
| | 500 | 0 | 557 | 0 |
| | 1000 | 0 | 854 | 0 |
| | 1500 | 0 | 1126 | 0 |

TABLE 12

Conversion of 200 mM HMB-Nitrile to HMB-Amide by Strain 52 in the Presence of Various Amide Concentrations

| | Product Observed, mM | | |
|---|---|---|---|
| Initial Amide, mM | HMB-Nitrile | HMB-Amide | HMB-Acid |
| 0 | 0 | 22 | 158 |
| 200 | 0 | 324 | 50 |
| 500 | 27 | 617 | 0 |
| 1000 | 127 | 807 | 0 |
| 1500 | 141 | 1172 | 0 |

In another set of experiments, HMB-nitrile was enzymatically hydrated with initial HMB-amide concentrations in the reaction mixture of 0 mM, 100 mM, 250 mM, 500 mM, 750 mM, 1000 mM, 1250 mM and 1500 mM at a temperature of about 28° C. The concentration of nitrile remaining at various times during the reaction was determined (FIG. 7A) and the corresponding initial reaction rates were calculated (FIG. 7B). While the nitrile hydratase activity declined with increasing HMB-amide concentration, measurable activity existed even in the presence of saturated HMB-amide. Specifically, in a reaction solution having an initial HMB-nitrile concentration of about 100 mM and an HMB-amide concentration of about 1M, the specific activity averaged over the first 5 minutes was about 66 $\mu$mole·min$^{-1}$/g dry cell, the specific activity averaged over the first 10 minutes was about 49 $\mu$mole·min$^{-1}$/g dry cell, the specific activity averaged over the first 20 minutes was about 46 $\mu$mole·min$^{-1}$/g dry cell and the specific activity averaged over the first hour was about 19 $\mu$mole·min$^{-1}$/g dry cell. In a reaction solution having an initial HMB-nitrile concentration of about 100 mM and an HMB-amide concentration of about 1.25M, the specific activity averaged over the first 5 minutes was about 40 $\mu$mole·min$^{-1}$/g dry cell, the specific activity averaged over the first 10 minutes was about 39 $\mu$mole·min$^{-1}$/g dry cell, the specific activity averaged over the first 20 minutes was about 43 $\mu$mole·min-min$^{-1}$/g dry cell and the specific activity averaged over the first hour was about 19 $\mu$mole·min$^{-1}$/g dry cell. In a reaction solution having an initial HMB-nitrile concentration of about 100 mM and an HMB-amide concentration of about 1.5M, the specific activity averaged over the first 5 minutes was about 60 $\mu$mole·min$^{-1}$/g dry cell, the specific activity averaged over the first 10 minutes was about 30 $\mu$mole·min$^{-1}$/g dry cell, the specific activity averaged over the first 20 minutes was about 38 $\mu$mole·min$^{-1}$/g dry cell and the specific activity averaged over the first hour was about 18 $\mu$mole·min$^{-1}$/g dry cell. The reaction rate in 1500 mM amide was approximately three-fold less than that observed in the absence of HMB-amide. (FIG. 7B). Moreover, in experimental runs in which a hydration reaction was carried out in the initial absence of HMB-amide with an initial HMB-nitrile concentration of about 100 mM, the initial specific activity was calculated to be about 700 $\mu$mole min$^{-1}$/g dry cell. (Example 6, Table 10). Hence, the initial specific activity of strain 52 or 56 wt cells in a reaction solution saturated with HMB-amide is expected to be at least about 50 $\mu$mole·min$^{-1}$/g dry cell, more likely at least about 100 $\mu$mole·min$^{-1}$/g dry cell and even more likely at least about 200 $\mu$mole·min$^{-1}$/g dry cell.

In a separate set of experiments, the amidase activity was relatively more sensitive to 2-hydroxy-4-(methylthio)-butaneamide as compared to the nitrile hydratase activity. Maximum amidase activities were observed at HMB-amide concentrations ranging from about 50 mM to about 75 mM. Activities of about one-half of the maximum amidase activities were observed, on the low end, at HMB-amide concentrations ranging from about 5 mM to about 10 mM, and on the high end, at HMB-amide concentrations of about 400 mM.

Example 9

Effect of Ammonium Salt of 2-Hydroxy-4-(methylthio)-butanoic acid on Nitrile Hydratase and Amidase Activities Nitrile hydratase activity is relatively independent of inhibition by ammonium salts of 2-hydroxy-4-(methylthio)-butanoic acid (HMB-acid). The effects of various concentrations of the ammonium salt of HMB-acid on the activities of strains 52 and 56 wt were evaluated. The assays were conducted for one hour at 30° C. As shown in Table 13, the nitrile hydratase from strain 52 was active even in the presence of 1M ammonium HMB-acid salt (152 $\mu$mole·min$^{-1}$/g dry cells). The results for strain 56 wt were consistent with these data.

TABLE 13

Inhibition of HMB-Nitrile Hydratase and HMB-Amidase of Strain 52 by HMB-Acid Salt

| Substrate | HMB-Acid Concentration mM | Substrate Consumed, mM | Apparent Percent Relative Activity |
|---|---|---|---|
| HMB-Nitrile | 0 | 103.5 | 100 |
|  | 100 | 103.2 | 99.7 |
|  | 200 | 105.2 | 102 |
|  | 500 | 105.6 | 102 |
|  | 1000 | 94.0 | 91 |
| HMB Amide | 0 | 60.5 | 100 |
|  | 100 | 30.9 | 51 |
|  | 200 | 56.0 | 92 |
|  | 500 | 0 | 0 |
|  | 1000 | 0 | 0 |

The amidases, on the other hand were inhibited by the ammonium salt of HMB-acid (Table 13). At 100–200 mM HMB-acid, the enzymes were approximately 50% as active as in the absence of HMB-acid, and inhibition was virtually complete at 500 mM HMB-acid. Control experiments showed that the inhibition was, in fact, due to HMB-acid rather than ammonium: (1) amidase assays performed in the presence of the sodium salt of HMB-acid were quantitatively similar to those performed in the presence of the ammonium salt thereof; and (2) no amidase inhibition was observed in the presence of 0.5M ammonium chloride.

Example 10

Effect of Cell Concentration on Nitrile Hydratase Activity

Figure 8:
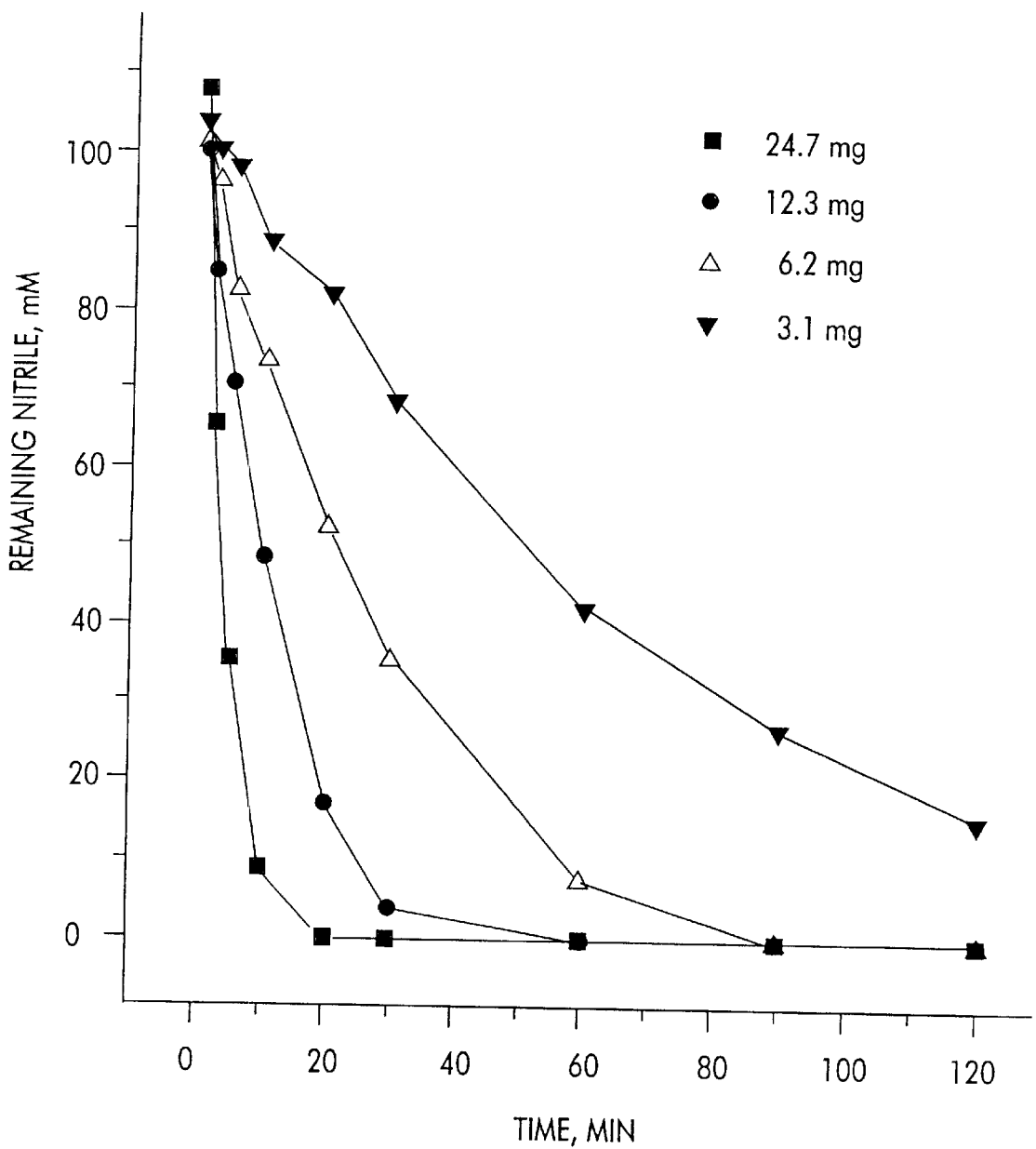
FIG. 8 is a graph showing the reaction progress for the bioconversion of untreated 2-hydroxy-4-(methylthio)-butanenitrile (HMB-nitrile) to HMB-amide using various concentrations of strain 52 whole cells in the reaction mixture (24.7 mg/ml, 12.3 mg/ml, 6.2 mg/ml and 3.1 mg/ml) based on dry weight of biocatalyst per milliliter of reaction mixture.

Nitrile hydratase activity increases with increasing cell concentration. For these studies, a culture of strain 52 was grown in the previously described manner and a concentrated cell suspension was prepared in 0.1M Na$_2$HPO$_4$/KH$_2$PO$_4$, pH 7.1. Serial dilutions of the cell suspension were prepared for use in hydrating 2-hydroxy-4-(methylthio)-butanenitrile (HMB-nitrile) in 1 ml reactions. The concentration of cells in the reaction mixtures, based on dry weight of biocatalyst per milliliter of reaction mixture, was 24.7 mg/ml, 12.3 mg/ml, 6.2 mg/ml and 3.1 mg/ml for the various runs. Nitrile hydratase activity was monitored over relatively short time intervals. The results, presented in FIG. 8 and Table 14, indicate that the initial rate of reaction was approximately proportional to the catalyst concentration, as expected for an enzyme. The specific activities decreased with time, most likely due to substrate inhibition, (Example 7), but were relatively independent of cell concentrations, except at a low concentration (3.1 mg/ml).

TABLE 14

Nitrile Hydratase Activity of
Strain 52 as a Function of Cell Density

| Cell Concentration, mg/mL | Reaction Rate, mmol min$^{-1}$ mL$^{-1}$ | Specific Activity, mmol min$^{-1}$ gram dry weight$^{-1}$ |
| --- | --- | --- |
| 24.7 | 14.6 | 590 |
| 12.3 | 6.0 | 490 |
| 6.2 | 3.8 | 620 |
| 3.1 | 1.2 | 380 |

Example 11

Effect of Temperature on the Stability of Nitrile Hydratase Activity

Figure 9B:
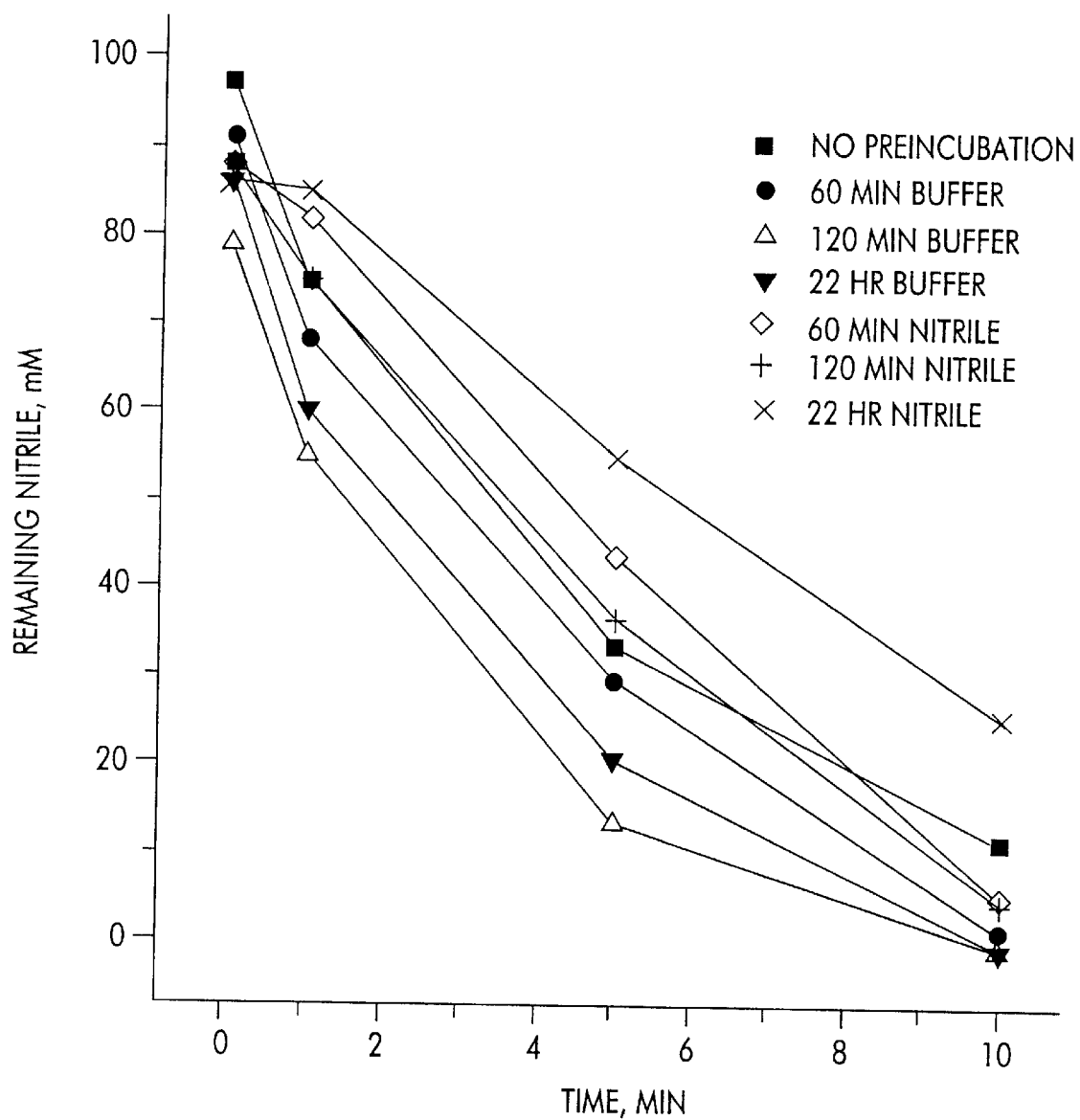

Experimental data indicate that lower temperatures generally lead to increased stability of nitrile hydratase activity for the conversion of 2-hydroxy-4-(methylthio)-butanenitrile (HMB-nitrile) to its corresponding amide. Strain 52 cells were preincubated for various times in either buffer solution (0.1M Na$_2$HPO$_4$/KH$_2$PO$_4$, pH 7.1) or in 100 mM nitrogen-purged HMB-nitrile at a temperature of either 22° C. or, in separate runs, 2.5° C. The cells were then washed and used as a biocatalyst for the hydration of HMB-nitrile. The results, shown in FIGS. 9A and 9B for the runs conducted at 22° C. and at 2.5° C., respectively, indicate that the activity of the nitrile hydratase was more stable in the presence of HMB-nitrile at lower temperatures as compared to higher temperatures. When cells were incubated with HMB-nitrile for 22 hours at 22° C., almost no nitrile hydratase activity was observed, In contrast, only a 50% reduction in activity was observed for cells incubated with HMB-nitrile for 22 hours at 2.5° C.

Example 12

Effect of Temperature on Nitrile Hydratase Activity for Untreated and Nitrogen-Purged HMB-nitrile Strain 52 whole cells were cultured, washed, concentrated 35 to 40-fold and incubated in 0.1M Na$_2$HPO$_4$/KH$_2$PO$_4$ buffer (pH 7.1). 2-Hydroxy-4-(methylthio)-butanenitrile (HMB-nitrile), either untreated or nitrogen-sparged, was added to a biochemical reactor supplied with an aqueous suspension of the strain 52 cells. The concentration of HMB-nitrile was kept below a maximum desired level ranging from about 50 mM to about 200 mM, depending on the experiment. As shown in Table 15, the reactions were carried using either untreated or nitrogen-purged HMB-nitrile at various temperatures (2.5° C., 6.5° C. or 28° C.). The concentration of the HMB-nitrile substrate was monitored by HPLC, and additional HMB-nitrile was added when the concentration decreased substantially.

TABLE 15

Summary of Bioreactor Experiments

| HMB-Nitrile | Temp. °C. | Final Amide Concentration, mM | Comments |
| --- | --- | --- | --- |
| Untreated | 28 | 200 | Catalyst unstable. 100 mM HMB-acid formed. |
| Untreated | 6.5 | 500 | Slower initial rate, but catalyst more stable. No HMB-acid. |
| N$_2$- purged | 28 | 430 | Faster reaction and more stable than with untreated nitrile, however catalyst still unstable. HMB-acid formed. |
| N$_2$- purged | 6.5 | 730 | Greater stability and no HMB-acid compared with 28° C. experiment. |
| N$_2$- purged | 2.5 | 1,020 | Reaction carried past amide saturation point. HMB-Amide crystals observed. |

The results, summarized in Table 15, demonstrate that the use of nitrogen-purged HMB-nitrile led to a faster reaction, improved HMB-amide yields and greater catalyst stability as compared to untreated HMB-nitrile substrate. This observation was consistent with observations presented in Example 7. Additionally, conducting the reaction at lower temperatures led to increased catalyst stability and decreased formation of HMB-acid relative to reactions carried out at higher temperatures. HMB-nitrile was efficiently hydrated at 6.5° C. and 2.5° C., with HMB-amide formation occurring at 2.5° C. even in the presence of saturating conditions of HMB-amide. The HMB-nitrile hydration at 28° C. was less stable in terms of the long-term nitrile hydratase activity of the whole-cell biocatalyst. Cells used in the reaction at 28° C. lacked observable nitrile hydratase activity when recovered from the reaction mixture by centrifugation, thoroughly washed and assayed therefore.

The supernatant of the centrifuged reaction product in the immediately preceding experiment was used in another experiment. Fresh cells were added to the reaction product supernatant. Nitrile hydratase activity was observed (as the disappearance of added HMB-nitrile) and HMB-amide crystals formed during a reaction initiated in a saturated HMB-amide solution and carried out at room temperature (22° C.).

Example 13

Biochemical Conversion of 2-Hydroxy-4-(methylthio)-butanenitrile (HMB-nitrile) to HMB-amide Under Saturated Amide Conditions Strain 52 cells from 200 ml of culture were harvested, washed twice with 0.1M Na$_2$HPO$_4$/KH$_2$PO$_4$ buffer (pH 7.1) and resuspended in 6 mL of the same buffer to give an aqueous cell suspension of 79 g/L (dry weight). The whole-cell suspension was supplied to a biochemical reactor, and after adding an additional 5 ml of the buffer, nitrogen-sparged 2-hydroxy-4-(methylthio)-butanenitrile (HMB-nitrile) was added to form a reaction solution with a final volume of about 12 ml. The reaction was carried out at a reaction temperature of about 6.5° C. The progress of the reaction was monitored by sampling the clear pale-yellow supernatant and determining HMB-nitrile concentration therein by HPLC. Additional HMB-nitrile was added periodically during the course of the reaction to maintain the concentration of HMB-nitrile in the reaction solution at about 50 mM or less. For the last three additions, the concentration of HMB-nitrile was 100 mM. Additional whole-cell suspension was added 3 hours, 5 hours and 9.5 hours after the start of the reaction in response to observed declines in activity. HMB-amide began precipitating at approximately 600 mM at about 4 hours after the start of the reaction.

Figure 10:
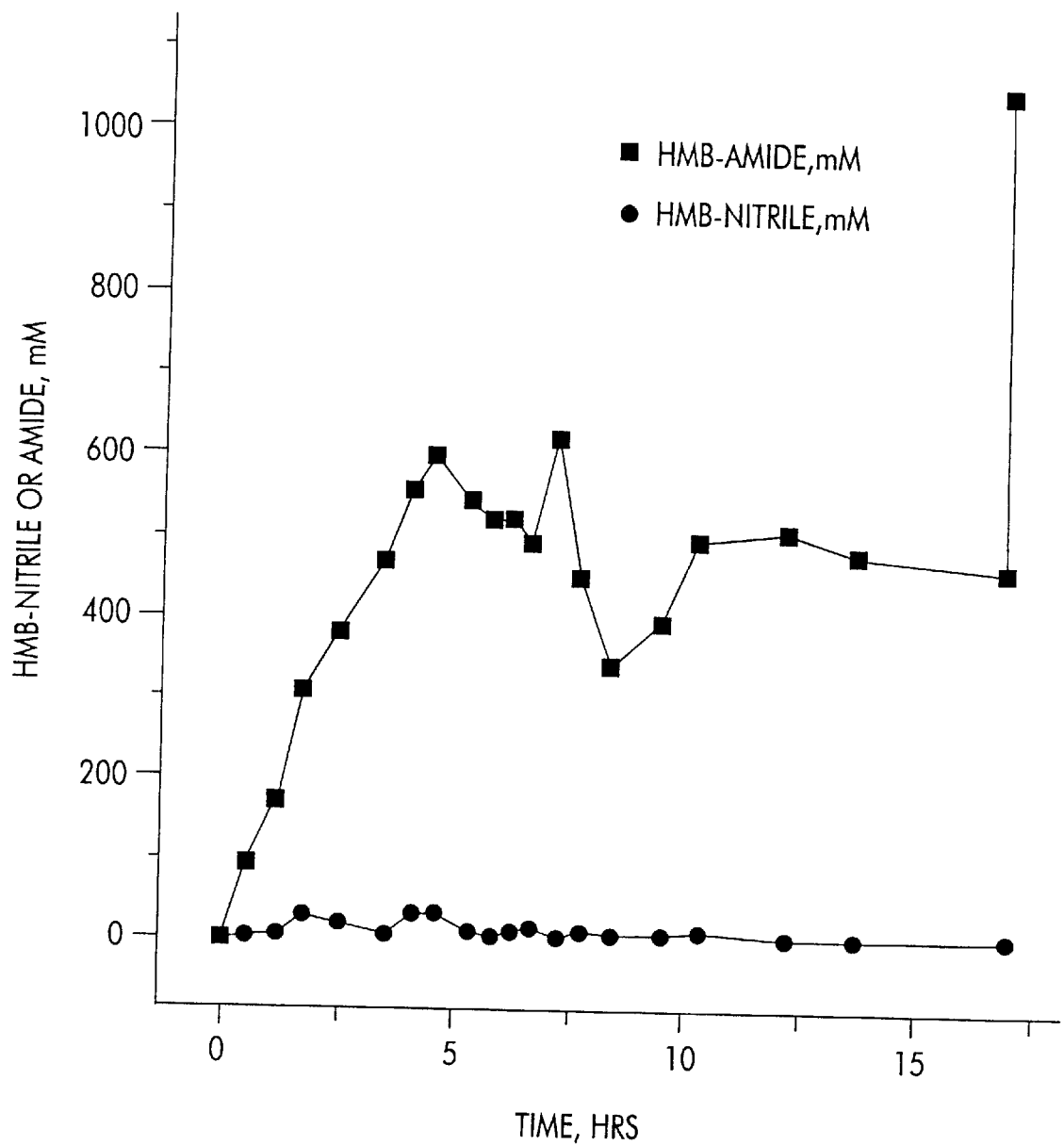
FIG. 10 is a graph showing the reaction progress for the bioconversion of 2-hydroxy-4-(methylthio)-butanenitrile (HMB-nitrile) to HMB-amide using an aqueous cell suspension of strain 52 whole cells (79 g/l dry weight) and nitrogen-sparged HMB-nitrile (<about 50 mM) at a reaction temperature of about 6.5° C.

FIG. 10 shows the concentration of HMB-amide and HMB-nitrile in the reaction supernatant over the course of the reaction. The concentration of HMB-amide product formed leveled off after about 4 hours as saturation conditions were established and HMB-amide crystals began to form. The average specific activity was determined to be about 100 $\mu$mol·min$^{-1}$/g dry cells during the first hour and about 35 $\mu$mol·min$^{-1}$/g dry cells over the course of the entire 17 hr reaction. The specific activity averaged over the 12 hour period during which the reaction solution was saturated with HMB-amide was about 31 $\mu$mol·min$^{-1}$/g dry cells. At the end of the process, the suspension was heated to 50° C. to dissolve the HMB-amide crystals. HPLC analysis of the sample taken subsequent to the redissolution of HMB-amide crystal is represented by the single high point on FIG. 10. The whole-cells were removed from the reaction mixture by centrifugation while the mixture was warm and the HMB-amide was dissolved. The final amide concentration of the supernatant was 1.12M. The supernatant was subsequently cooled to room temperature, resulting in recrystallization of HMB-amide. No residual HMB-nitrile or HMB-acid were detected in the product.

The experiment was repeated with essentially identical results.

In light of the detailed description of the invention and the examples presented above, it can be appreciated that the several objects of the invention are achieved. The examples, explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A process for the enzymatic conversion of a substituted or unsubstituted α-hydroxybutyronitrile to a corresponding α-hydroxybutyramide, the process comprising hydrating the α-hydroxybutyronitrile in the presence of a microbial enzyme to form the corresponding α-hydroxybutyramide, the enzyme having the capability of hydrating the α-hydroxybutyronitrile in a solution saturated with the α-hydroxybutyramide.

2. The process of claim 1 wherein the α-hydroxybutyronitrile is hydrated in an aqueous solution and the α-hydroxybutyramide is present in the solution at a concentration ranging from about 50% to 100% of its saturation concentration.

3. The process of claim 1 wherein the hydroxybutryonitrile is hydrated in the presence of microbial cells or a lysate thereof and the nitrile hydratase activity of the cells or cell lysate in an aqueous solution saturated with the α-hydroxybutyramide is at least about 20 $\mu$mole·min$^{-1}$/g dry cells averaged over a period of about one hour.

4. The process of claim 1 wherein the enzyme is derived from microbes of the genus Rhodococcus.

5. The process of claim 1 wherein the enzyme is derived from strains 52 or 56 wt, deposited with the American Type Culture Collection, Accession No. 55923 and Accession No. 55924, respectively.

6. The process of claim 1 wherein the α-hydroxybutyronitrile is 2-hydroxy-4-(methylthio)-butanenitrile.

7. A process for the bioconversion of a substituted or unsubstituted α-hydroxybutyronitrile to a corresponding α-hydroxybutyramide, the process comprising hydrating the α-hydroxybutyronitrile in the presence of microbial cells or a lysate thereof to form the corresponding α-hydroxybutyramide, the cells or cell lysate having the capability of hydrating the α-hydroxybutyronitrile in a solution saturated with the α-hydroxybutyramide.

8. The process of claim 7 wherein the α-hydroxybutyronitrile is hydrated in an aqueous solution and the α-hydroxybutyramide is present in the solution at a concentration ranging from about 50% to 100% of its saturation concentration.

9. The process of claim 7 wherein the nitrile hydratase activity of the cells or cell lysate in an aqueous solution saturated with the α-hydroxybutyramide is at least about 50 $\mu$mole·min$^{-1}$/g dry cells averaged over a period of about one hour.

10. The process of claim 7 wherein the nitrile hydratase activity of the cells or cell lysate in an aqueous solution saturated with the α-hydroxybutyramide is at least about 30 $\mu$mole·min$^{-1}$/g dry cells averaged over a period of about 12 hours.

11. The process of claim 7 wherein the microbial cells are of the genus Rhodococcus.

12. The process of claim 7 wherein the microbial cells are strains 52 or 56 wt, deposited with the American Type Culture Collection, Accession No. 55923 and Accession No. 55924, respectively.

13. The process of claim 7 wherein the microbial cells are immobilized on a solid support matrix.

14. The process of claim 7 wherein the α-hydroxybutyronitrile is 2-hydroxy-4-(methylthio)-butanenitrile.

15. The process of claim 7 wherein the α-hydroxybutyronitrile is hydrated in an aqueous solution having an amount of hydrogen cyanide which is equal to or less than about 0.5 mole % relative to the amount of α-hydroxybutyronitrile in the solution.

16. The process of claim 7 wherein the α-hydroxybutyronitrile is hydrated in a continuous stirred tank reactor.

17. A process for the enzymatic conversion of 2-hydroxy-4-(methylthio)-butanenitrile to 2-hydroxy-4-(methylthio)-butaneamide, the process comprising enzymatically hydrating 2-hydroxy-4-(methylthio)-butanenitrile in a reaction solution to form 2-hydroxy-4-(methylthio)-butaneamide, the 2-hydroxy-4-(methylthio)-butaneamide being present in the solution at a concentration ranging from about 50% to 100% of its saturation concentration.

18. The process of claim 17 wherein the concentration of 2-hydroxy-4-(methylthio)-butaneamide present in the reaction solution is at least about 300 mM.

19. The process of claim 17 wherein the concentration of 2-hydroxy-4-(methylthio)-butanoic acid present in the reaction solution is less than about 50 mM.

20. The process of claim 17 further comprising obtaining or preparing an aqueous cell suspension comprising whole cells of strains 52 or 56 wt, the cell strains being deposited with the American Type Culture Collection, Accession No. 55923 and Accession No. 55924, respectively, obtaining or preparing 2-hydroxy-4-(methylthio)-butanenitrile having less than about 0.5 mole % hydrogen cyanide present therein relative to the amount of 2-hydroxy-4-(methylthio)-butanenitrile, and combining the cell suspension with 2-hydroxy-4-(methylthio)-butanenitrile to form a reaction solution, the concentration of 2-hydroxy-4-(methylthio)-butanenitrile in the reaction solution being maintained at less than about 100 mM and the temperature of the reaction solution ranging from about 2° C. to about 30° C.

21. A process for the enzymatic conversion of an α-hydroxynitrile to a corresponding α-hydroxyamide, the process comprising obtaining or preparing α-hydroxynitrile having less than about 0.5 mole % hydrogen cyanide present therein relative to the amount of α-hydroxynitrile, and enzymatically hydrating the α-hydroxynitrile to form an α-hydroxyamide.

22. A process for the enzymatic conversion of an α-hydroxynitrile to a corresponding α-hydroxyamide, the process comprising removing hydrogen cyanide from a solution comprising α-hydroxynitrile and hydrogen cyanide to reduce the amount of hydrogen cyanide present in the solution, and enzymatically hydrating α-hydroxynitrile in the solution to form an α-hydroxyamide.

23. The process of claim 22 wherein the hydrogen cyanide is removed by contacting the solution with a stripping gas.

24. The process as set forth in claim 21 wherein the α-hydroxynitrile is an α-hydroxybutyronitrile.

25. The process of claim 21 wherein the α-hydroxynitrile is 2-hydroxy-4-(methylthio)-butanenitrile.

26. A process for the enzymatic conversion of a nitrile to a corresponding amide, the process comprising hydrating the nitrile in the presence of a microbial enzyme to form the corresponding amide, the enzyme being derived from microbial strains 52 or 56 wt deposited with the American Type Culture Collection, Accession No. 55923 and Accession No. 55924, respectively.

27. The process of claim 26 wherein the nitrile is an α-hydroxynitrile.

28. The process of claim 26 wherein the nitrile is a butyronitrile.

29. The process of claim 26 wherein the nitrile is an α-substituted-butyronitrile.

30. The process of claim 26 wherein the nitrile is an α-hydroxybutyronitrile.

31. The process of claim 26 wherein the nitrile is 2-hydroxy-4-(methylthio)-butanenitrile.

32. The process of claim 26 wherein the nitrile is an α-hydroxynitrile and is hydrated in an aqueous reaction solution in the presence of microbial cells or a lysate thereof and the nitrile hydratase activity of the cells or cell lysate in a reaction solution saturated with the corresponding α-hydroxyamide is at least about 20 μmole·min$^{-1}$/g dry cells over a period of about one hour.

33. The process of claim 26 wherein the nitrile is an α-hydroxynitrile and is hydrated in an aqueous reaction solution and the α-hydroxyamide is present in the reaction solution at a concentration ranging from about 50% to 100% of its saturation concentration.

34. The process of claim 26 wherein the nitrile is hydrated in the presence of strain 52 or 56 wt whole cells or lysates thereof.

35. A process for the enzymatic conversion of an amide to a corresponding carboxylic acid, the process comprising hydrolyzing the amide in the presence of a microbial enzyme to form the corresponding carboxylic acid, the enzyme being derived from strains 52 or 56 wt, deposited with the American Type Culture Collection, Accession No. 55923 and Accession No. 55924, respectively.

36. The process of claim 35 wherein the amide is an α-hydroxyamide.

37. The process of claim 35 wherein the amide is a butyramide.

38. The process of claim 35 wherein the amide is an α-substituted-butyramide.

39. The process of claim 35 wherein the amide is an α-hydroxybutyramide.

40. The process of claim 35 wherein the amide is 2-hydroxy-4-(methylthio)-butaneamide.

41. The process of claim 35 wherein the nitrile is hydrated in the presence of strain 52 or 56 wt whole cells or lysates thereof.

42. A process for the enzymatic conversion of a nitrile to a corresponding carboxylic acid, the process comprising hydrating the nitrile to form the corresponding amide, and hydrolyzing the amide to form the corresponding carboxylic acid, at least one of the hydration reaction and hydrolysis reaction being carried out in the presence of a microbial enzyme derived from strains 52 or 56 wt deposited with the American Type Culture Collection, Accession No. 55923 and Accession No. 55924, respectively.

43. The process of claim 42 wherein the nitrile is 2-hydroxy-4-(methylthio)-butanenitrile.

44. The process of claim 42 wherein the hydration and hydrolysis reactions are each carried out in the presence of a microbial enzyme.

45. The process of claim 42 wherein the nitrile is enzymatically hydrated in an aqueous solution and the amide is present in the solution at a concentration ranging from about 50% to 100% of its saturation concentration.

46. A process for the preparation of salts of 2-hydroxy-4-(methylthio)-butanoic acid from 2-hydroxy-4-(methylthio)-butanenitrile, the process comprising enzymatically hydrating 2-hydroxy-4-(methylthio)-butanenitrile to form 2-hydroxy-4-(methylthio)-butaneamide, and hydrolyzing the resulting 2-hydroxy-4-(methylthio)-butaneamide in a basic solution to form a salt of 2-hydroxy-4-(methylthio)-butanoic acid.

47. The process as set forth in claim 46 wherein 2-hydroxy-4-(methylthio)-butanenitrile is hydrated in the presence of an enzyme having the capability of hydrating 2-hydroxy-4-(methylthio)-butanenitrile in an aqueous solution saturated with 2-hydroxy-4-(methylthio)-butaneamide.

48. The process as set forth in claim 47 wherein 2-hydroxy-4-(methylthio)-butanenitrile is hydrated in the presence of microbial cells or a lysate thereof and the nitrile hydratase activity of the cells or cell lysate in an aqueous solution saturated with 2-hydroxy-4-(methylthio)-butaneamide is at least about 20 μmole·min$^{-1}$/g dry cells averaged over a period of about one hour.

49. The process of claim 46 wherein 2-hydroxy-4-(methylthio)-butanenitrile is hydrated in an aqueous solution and 2-hydroxy-4-(methylthio)-butaneamide is present in the solution at a concentration ranging from about 50% to 100% of its saturation concentration.

50. The process of claim 46 wherein the enzyme is derived from microbes of genus Rhodococcus.

51. The process of claim 46 wherein the enzyme is derived from strains 52 or 56 wt, deposited with the American Type Culture Collection, Accession No. 55923 and Accession No. 55924, respectively.

52. The process of claim 46 wherein the nitrile is hydrated in the presence of microbial whole cells or lysates thereof.

53. An isolated and substantially purified microorganism designated herein as strain 52 and deposited with the American Type Culture Collection, Accession No. 55923.

54. An isolated and substantially purified microorganism designated herein as strain 56 wt and deposited with the American Type Culture Collection, Accession No. 55924.

55. The process as set forth in claim 21 wherein the α-hydroxynitrile is enzymatically hydrated in the presence of microbial whole cells or lysates thereof.

56. The process as set forth in claim 42 wherein at least one of the hydration reaction and the hydrolysis reaction are carried out in the presence of strain 52 or 56 wt whole cells or cell lysates thereof.

57. The process of claim 2 wherein the enzyme is derived from microbes of the genus Rhodococcus.

58. The process of claim 2 wherein the α-hydroxybutyronitrile is 2-hydroxy-4-(methylthio)-butanenitrile.

59. The process of claim 8 wherein the enzyme is derived from microbes of the genus Rhodococcus.

60. The process of claim 8 wherein the microbial cells are immobilized on a solid support matrix.

61. The process of claim 8 wherein the α-hydroxybutyronitrile is 2-hydroxy-4-(methylthio)-butanenitrile.

62. The process as set forth in claim 21 wherein the amount of hydrogen cyanide in the solution is reduced to less than about 0.5 mole % hydrogen cyanide relative to the amount of α-hydroxynitrile.

63. The process of claim 21 wherein the hydrogen cyanide is removed from the solution by contacting the α-hydroxynitrile with a stripping gas to reduce the amount of hydrogen cyanide present in the solution to less than about 0.5 mole % hydrogen cyanide relative to the amount of α-hydroxynitrile.

64. A process for the enzymatic conversion of an α-hydroxynitrile to a corresponding α-hydroxyamide, the process comprising enzymatically hydrating α-hydroxynitrile in a reaction solution having less than about 0.5 mole % hydrogen cyanide relative to the amount of α-hydroxynitrile in the reaction solution.

* * * * *